United States Patent
Hangartner et al.

(10) Patent No.: US 9,512,202 B2
(45) Date of Patent: Dec. 6, 2016

(54) MULTI-STRAIN-REACTIVE ANTIBODIES FOR THERAPY AND DIAGNOSIS OF INFLUENZA

(75) Inventors: Lars Hangartner, Schaffhausen (CH); Arkadiusz Wyrzucki, Zurich (CH)

(73) Assignee: UNIVERSITY OF ZURICH, Zurich (CH)

( * ) Notice: Subject to any disclaimer, the term of this patent is extended or adjusted under 35 U.S.C. 154(b) by 47 days.

(21) Appl. No.: 14/241,114

(22) PCT Filed: Aug. 27, 2012

(86) PCT No.: PCT/EP2012/066626
§ 371 (c)(1),
(2), (4) Date: Feb. 26, 2014

(87) PCT Pub. No.: WO2013/030165
PCT Pub. Date: Mar. 7, 2013

(65) Prior Publication Data
US 2014/0370032 A1      Dec. 18, 2014

(30) Foreign Application Priority Data

Sep. 2, 2011 (EP) .................................. 11179955

(51) Int. Cl.
| | | |
|---|---|---|
| *C07K 16/10* | (2006.01) | |
| *A61K 39/145* | (2006.01) | |
| *G01N 33/566* | (2006.01) | |
| *G01N 33/569* | (2006.01) | |
| *A61K 39/12* | (2006.01) | |
| *A61K 39/00* | (2006.01) | |

(52) U.S. Cl.
CPC ......... *C07K 16/1018* (2013.01); *A61K 39/12* (2013.01); *A61K 39/145* (2013.01); *G01N 33/566* (2013.01); *G01N 33/56983* (2013.01); *A61K 2039/505* (2013.01); *A61K 2039/545* (2013.01); *A61K 2039/70* (2013.01); *C07K 2317/21* (2013.01); *C07K 2317/76* (2013.01); *C12N 2760/16134* (2013.01); *C12N 2760/16234* (2013.01); *G01N 2469/10* (2013.01)

(58) Field of Classification Search
None
See application file for complete search history.

(56) References Cited

U.S. PATENT DOCUMENTS

2011/0274702 A1    11/2011    Lanzavecchia

FOREIGN PATENT DOCUMENTS

| WO | WO 2009/079259 | 6/2009 |
|---|---|---|
| WO | WO 2009/121004 | 10/2009 |
| WO | WO 2010/010466 | 1/2010 |
| WO | WO 2010/027818 | 3/2010 |

OTHER PUBLICATIONS

Kalenik et al., Acta Biochemica Polonica, 2014, 61(3):573-587.*
Corti D et al: "A Neutralizing Antibody Selected from Plasma Cells That Binds to Group 1 and Group 2 Influenza A Hemagglutinins", Science, vol. 333, No. 6044, Aug. 12, 2011, pp. 850-856.
Hoogenboom H R: "Selecting and screening recombinant antibody libraries", Nature Biotechnology, vol. 23, No. 9, Sep. 1, 2005, pp. 1105-1116.

* cited by examiner

*Primary Examiner* — Stacy B Chen
(74) *Attorney, Agent, or Firm* — JMB Davis Ben-David

(57) ABSTRACT

The invention relates to a method for isolating a polypeptide reactive to influenza A hemagglutinin, comprising the steps of preparing a library of nucleic acid sequences, wherein each member of said library is attached to a polypeptide sequence encoded thereby, selecting members of said library by contacting the members with a panning antigen, wherein the panning antigen comprises a hemagglutinin stem region polypeptide sequence, subsequently removing members unreactive to the panning antigen, and selecting a member of said library by determining its binding to at least 5 influenza A hemagglutinin subtypes of subtype group 1 and 2. The invention further relates to polypeptides, particularly antibodies, obtainable by this method, that neutralize at least five influenza A subtypes of subtype group 1 and 2, to vaccines and uses thereof.

9 Claims, 5 Drawing Sheets

MULTI-STRAIN-REACTIVE ANTIBODIES FOR THERAPY AND DIAGNOSIS OF INFLUENZA

CROSS-REFERENCE TO RELATED APPLICATIONS

This is the U.S. National Stage of International Application No. PCT/EP2012/066626, filed Aug. 27, 2012, which was published in English under PCT Article 21(2), which in turn claims the benefit of European Patent Application No. 11179119.0, filed Aug. 27, 2011 and European Patent Application No. 11179955.7, filed Sep. 2, 2011.

The present invention relates to polypeptides reactive against influenza A hemagglutinin, in particular antibodies, methods for discovery and use thereof, and vaccines. The invention further relates to an antigen engineered to elicit an immune response reactive against multiple strains of influenza, and the use of such antigen as a vaccine.

Development of vaccines to influenza A viruses is complicated by the virus' genetic variability and flexibility, which rapidly render pre-existing humoral immunity ineffective. A number of serological subtypes of influenza A viruses have emerged differing in their composition of hemagglutinin (HA), and neuraminidase (N) surface proteins. HA, and to a lesser extent N, constantly change as the result of immune pressure in a process termed antigenic drift.

The antigenic variability of the influenza A surface proteins arises from domains that can easily be altered without destroying the virus' cell attachment, entry or release abilities. In addition, these variable domains have evolved to be highly immunogenic and the resulting immunodominance indirectly protects the conserved and functionally critical regions of the virus surface from immune recognition. As a consequence, the vast majority of antibodies mounted during natural infection are highly strain-specific and their protective capacity can easily be evaded by a slight modification of the variable features of the virus surface.

Currently, there are 16 distinct subtypes known for HA. These subtypes also correspond to at least 16 distinct serotypes, i.e. that hyperimmune serum against one subtype fails at neutralizing viruses belonging to other serotypes. The HA subtypes can be divided into two groups. Within group 1, two clades of HA subtypes can be distinguished, namely the H1 clade (H1, H2, H5, H6, H11, H13, H16) and the H9 clade (H8, H9, H12). The first clade can be further subdivided into the H1a (H1, H2, H5, H6) and H1b (H11, H13, H16) subclades. The subtypes belonging to group 2 split up into the H3 (H3, H4, H14) and the H7 (H7, H10, H15) clades. Although only H1, H2 and H3 viruses have established themselves in humans, zoonotic infections with members of the other subtypes (of both groups) can be observed on a regular basis (H5N1, H7N3, H9N2, H10N7).

The course of most of these infections is mild, with the exception of zoonotic H5N1-expressing avian viruses that are characterized by over 60% lethality. Although zoonotic infections are typically not transmittable from human to human, any species transgression of influenza A viruses imposes the risk that the zoonotic virus acquires the ability for human to human transmission, either by adaptation, or by reassortment with human viruses. Such viruses would be likely to cause an influenza pandemic.

Heterosubtypic antibodies, i.e. antibodies that recognize HA from more than one HA subtype are rare and it has been estimated that such antibodies only occur at very low frequency in the human B cell memory pool (i.e. 320-16680 cells per million IgG+B cells). It has been demonstrated that only about ~0.01% of the total immunoglobulin of commercially available IgG preparations can bind and neutralize heterologous avian H5-expressing viruses.

Over the past 5 years, several heterosubtypic antibodies have been isolated from human donors either by phage display (M. Throsby et al., PLoS One 3, e3942 (2008)), or by single cell PCR from plasmablasts or memory B cells. Most of these antibodies were either specific for HA subtypes of group 1 or group 2 but not for both. In contrast to strain-specific antibodies that bind to epitopes located on the globular head of the hemagglutinin protein, and that therefore interfere with receptor binding, heterosubtypic antibodies were found to bind a conserved epitope in the stalk of the HA protein. Accordingly, these antibodies were found not to interfere with receptor binding but to impede conformational changes in HA required for fusion of the endosomal membrane with the viral envelope.

Of note is also the fact that most human heterosubtypic neutralizing antibodies isolated so far are encoded by variable region germline gene IGHV1-69 (V1-69), and that they all make contact to the same conserved area in the stem of the HA protein, i.e. between aa 291 and 321 of HA1 as well as aa 17 through 21 and aa 38-58 of HA2. HA1 and HA2 are disulfide linked polypeptide chains that are formed during maturation of hemagglutinin by proteolytic cleavage. HA1 contains the sialic acid receptor binding domain, whereby HA2 comprises the core fusion machinery on the stalk or stem region. Also quite unusual is the observation that these V1-69 encoded antibodies do not contact their epitope via complementarity determining regions 3 (CDR-H3) that arises from joining the V(D)J segments of the variable region and that typically provides several key residues contacting the epitope, but instead make the contacts mainly via the germline gene-derived CDR1 and CDR2 of the heavy chain. The light chain appears not to contribute to the binding energy of these heterosubtypic antibodies.

All heterosubtypic antibodies comprising a V1-69-encoded sequence published so far only neutralize influenza A viruses expressing HA subtypes belonging to group 1.

This discrimination between the two HA groups has been attributed to two main differences in the stem of hemagglutinin. First, position 38, located in HA1 in close proximity to the residues contacted by heterosubtypic antibodies, is glycosylated in group 2 HA subtypes, and has been postulated to sterically interfere with binding of antibodies to this epitope. Second, the side chain of tryptophan 21, which lies in the center of the characterized epitopes, is turned through 90° in group 2 HA subtypes and adopts a conformation that is supposed to clash with binding of the CDR-H1 of V1-69 antibodies. It has therefore been speculated that the V1-69 germline gene will not be able to encode for antibodies that recognize both group 1 and group 2 HA subtypes (Ekiert et al. *Science,* 324, 246-251, 2009, Ekiert et al. *Science,* DOI: 10.1126/science.1204839, 2011).

Based on this background the objective of the present invention is to provide multi-strain reactive antibodies for prevention, therapy and diagnosis of influenza A virus infections.

The present invention is based on surprising finding that heterospecific antibodies reactive against Influenza A virus strains of subtype groups 1 and 2 can be isolated from a library of polypeptide sequences, in particular libraries obtained from B-cells isolated from individuals previously exposed to influenza A hemagglutinin, by selecting heterospecific antibodies from naïve or—preferably—biased polypeptide libraries, using a HA-stem-region antigen derived from certain viral strains as selection agent.

According to a first aspect of the invention, a method for isolating a polypeptide reactive to influenza A hemagglutinin is provided, comprising the steps of:

preparing a library of nucleic acid sequences in a library preparation step, wherein each member of the library is attached to a polypeptide sequence encoded by the nucleic acid of said member;

selecting members of said library by contacting said members with a panning antigen in a binding step, wherein said panning antigen comprises a hemagglutinin stem region polypeptide sequence, and subsequently removing members unreactive to the panning antigen in a washing step;

selecting a member of said library by determining its binding to at least 2 influenza A hemagglutinin group 1 subtypes and 2 influenza A hemagglutinin group 2 subtypes in an antibody selection step.

According to a preferred embodiment, the panning antigen is a hemagglutinin polypeptide having an exposed stem region polypeptide sequence and a dampened apical polypeptide sequence.

The term "polypeptide reactive to influenza A hemagglutinin" in the sense of the invention refers to a polypeptide which is capable of specifically binding, at a dissociation rate of $10^{-7}$ mol/l or lower (nanomolar affinity), to an influenza A hemagglutinin and which is additionally capable of neutralizing the hemagglutinin. Neutralizing or neutralization in the sense of the invention means inhibiting the biological or pathogenic activity of hemagglutinin, thereby inhibiting the proliferation of influenza A viruses.

The term "members unreactive to panning antigen" refers to nucleic acids encoding polypeptides that do not specifically bind to the panning antigen and that can be removed in one or several washing steps.

The term "influenza A virus" includes, without being restricted to, influenza A viruses strains from subtype group 1 (H1, H2, H5, H6, H8 H9, H11, H12, H13, H16) and subtype group 2 (H3, H4, H7, H10, H14, H15), and in particular the influenza A virus strains H1N1, H2N2, H3N2, H4N6, H5N3, H6N1, H7N7, H8N4, H10N7, and H14N5.

The term "hemagglutinin stem region" refers to amino acid (aa) positions 1 to 52 and aa 277 to aa 328 of HA1, and the extracellular part of HA2, i.e. aa 1 to 175 (H3 numbering).

The term "apical region" refers to the part of HA1 that lies between Cys 52 and Cys 277. A dampened apical peptide sequence in the context of the present invention refers to an apical sequence section of the HA molecule, wherein the amino acids exposed on the apex of the native HA molecule, facing away from the longitudinal axis of the HA globular structure are restricted from access by immunoglobulin polypeptides or other binders. The apical polypeptide sequence contains the strain- or subtype specific binding sites. These are rendered inaccessible by dampening during the binding step, thus restricting subtype-specific epitope recognizing antibodies from binding to the panning antigen and being selected.

Dampening can be achieved by methods known in the art, such as glycosylation, chemical modification, deletion or mutagenesis or—as is preferred in the context of the present invention—by attachment of the HA polypeptide through the apical region to a globular structure or surface by a tether sufficiently short as to not allow access of binding polypeptides to epitopes in the apical region.

A library according to the first aspect of the invention may be a collection of bacteriophages, bacterial or yeast cells comprising the nucleic acid attached to an encoded polypeptide, wherein individual clones of phages, bacterial or yeast cells carry individual sequences of polypeptides to be selected. Alternatively, a library may be a collection of cDNAs or mRNAs, which can be transcribed or translated in vitro, and wherein the resulting translated polypeptide is connected to a coding nucleic acid.

A method for selecting members of a library in the binding step according to the first aspect of the invention, may be a suitable in vitro selection method such as phage display, bacterial display, yeast display, ribosome display or mRNA display, wherein a nucleic acid is connected to an encoded polypeptide sequence and selection is determined by the ability of the polypeptide to bind to the panning antigen. Phage display is a preferred method. A description of the phage display method can be found in Barbas et al. *Phage Display: A Laboratory Manual*. Cold Spring Harbour Laboratory Press, Cold Spring Harbor, N.Y.

Additionally, a method according to the first aspect of the invention may include reiterative rounds of evolution, whereby after one or several binding and washing steps, the selected members are submitted to a mutagenesis or recombination step, and subsequently the amino acid sequence or its encoding nucleotide sequence are selected, for identification of higher reactive polypeptides.

The method achieves the selection of polypeptides, particularly antibodies, reactive to influenza A hemagglutinin of both group 1 and group 2 subtypes by determining the selected members' ability to bind to at least two subtype specific HA molecules of each subtype group 1 and 2. This antibody selection step can be achieved as one or several rounds of "panning", i.e. as a sequence of antibody selection steps whereby members selected in repeated binding and washing steps are contacted with HA molecules of a specific subtype group X HA, another (different) subtype group X HA, then with HA molecules of a specific subtype group Y HA and finally another (different) subtype group Y HA. Subtype group X and Y refer to subtype group 1 and 2, interchangeably. The sequence may also be X-Y-X-Y or X-Y-Y-X, or more subtypes of either group 1 or 2 or both may be added.

Alternatively, the antibody selection step may be performed by simply isolating selected members after the last washing step and performing a selection on isolated members by conventional testing of the selected members'—or their encoded isolated polypeptides'—binding specificity.

According to some embodiments, a member of said library is selected by determining its binding to the group 1 subtypes H1, H2, H5 and/or H6, and to group 2 subtypes H3, H4, H7 and/or H10.

In some embodiments, a member of said library is selected by determining its binding to 2 group 1 subtypes and 5 or 6 group 2 subtypes, or 3 group 1 subtypes and 5 or 6 group 2 subtypes, or 4 group 1 subtypes and 2, 3, 4, 5 or 6 group 2 subtypes, or 5 group 1 subtypes and 2, 3, 4, 5 or 6 group 2 subtypes, or 6 group 1 subtypes and 2, 3, 4, 5 or 6 group 2 subtypes, or 7 group 1 subtypes and 2, 3, 4, 5 or 6 group 2 subtypes, or 8 group 1 subtypes and 2, 3, 4, 5 or 6 group 2 subtypes, or 9 group 1 subtypes, and 2, 3, 4, 5 or 6 group 2 subtypes in the antibody selection step.

According to some embodiments, where 2 group 1 subtypes are mentioned above, the combination is H1 and H2;

or H1 and H5; or H1 and H6; or H1 and H8; or H1 and H9; or H1 and H11; or H1 and H12; or H1 and H13; or H2 and H5; or H2 and H6; or H2 and H8; or H2 and H9; or H2 and H11; or H2 and H12; or H2 and H13; or H5 and H6; or H5 and H8; or H5 and H9; or H5 and H11; or H5 and H12; or H5 and H13; or H6 and H8; or H6 and H9; or H6 and H11; or H6 and H12; or H6 and H13; or H8 and H9; or H8 and H11; or H8 and H12; or H8 and H13; or H9 and H11; or H9 and H12; or H9 and H13; or H11 and H12; or H11 and H13; or H12 and H13.

Similarly, where 2 group 2 subtypes are mentioned above, the combination in some embodiments is H3 and H4, or H3 and H7, or H3 and H10, or H3 and H14, or H3 and H15, or H4 and H7, or H4 and H10, or H4 and H14, or H4 and H15, or H7 and H10, or H7 and H14, or H7 and H15, or H10 and H14, or H10 and H15, or H14 and H15;

where 3 group 1 subtypes are mentioned, the combination is H1, H2 and H5; or H1, H2 and H6; or H1, H2 and H8; or H1, H2 and H9; or H1, H2 and H11; or H1, H2 and H12; or H1, H2 and H13; or H1, H5 and H8; or H1, H5 and H9; or H1, H5 and H11; or H1, H5 and H12; or H1, H5 and H13; or H1, H8 and H9; or H1, H8 and H11; or H1, H8 and H12; or H1, H8 and H13; or H1, H9 and H11; or H1, H9 and H12; or H1, H9 and H13; or H1, H11 and H12; or H1, H11 and H13; or H1, H12 and H13; or H2, H5 and H6; or H2, H5 and H8; or H2, H5 and H9; or H2, H5 and H11; or H2, H5 and H12; or H2, H5 and H12; or H2, H5 and H13; or H2, H6 and H8; or H2, H6 and H9; or H2, H6 and H11; or H2, H6 and H12; or H2, H6 and H13; or H2, H8 and H9; or H2, H8 and H11; or H2, H8 and H12; or H2, H8 and H13; or H2, H9 and H11; or H2, H9 and H12; or H2, H9 and H13; or H2, H11 and H12; or H2, H11 and H13; or H2, H12 and H13; or H5, H6 and H8; or H5, H6 and H9; or H5, H6 and H11; or H5, H6 and H12; or H5, H6 and H13; or H5, H8 and H9; or H5, H8 and H11; or H5, H8 and H12; or H5, H8 and H13; or H5, H9 and H11; or H5, H9 and H12; or H5, H9 and H13; or H5, H11 and H12; or H5, H11 and H13; or H5, H12 and H13; or H6, H8 and H9; or H6, H8 and H11; or H6, H8 and H12; or H6, H8 and H13; or H6, H9 and H11; or H6, H9 and H12; or H6, H9 and H13; or H6, H11 and H12; or H6, H11 and H13; or H6, H12 and H13; or H8, H9 and H11; or H8, H9 and H12; or H8, H9 and H13; or H8, H11 and H12; or H8, H11 and H13; or H8, H12 and H13; or H9, H11 and H12; or H9, H11 and H13; or H9, H12 and H13; or H11, H12 and H13;

where 3 group 2 subtypes are mentioned, some embodiments provide the combinations H3, H4 and H7; or H3, H4 and H10; or H3, H4 and H14; or H3, H4 and H15; or H3, H7 and H10; or H3, H7 and H14; or H3, H7 and H15; or H3, H10 and H14; or H3, H10 and H15; or H3, H14 and H15; or H4, H7 and H10; or H4, H7 and H14; or H4, H7 and H15; or H7, H10 and H14; or H7, H10 and H15; or H10, H14 and H15;

where 4 group 1 subtypes are mentioned, the combination in some embodiments is H1, H2, H5 and H6, or H1, H2, H5 and H8, or H1, H2, H5 and H9, or H1, H2, H5 and H11, or H1, H2, H5 and H12, or H1, H2, H5 and H13, or H1, H2, H6 and H8, or H1, H2, H6 and H9, or H1, H2, H6 and H11, or H1, H2, H6 and H12, or H1, H2, H6 and H13, or H1, H2, H8 and H9, or H1, H2, H8 and H11, or H1, H2, H8 and H12, or H1, H2, H8 and H13, or H1, H2, H9 and H11, or H1, H2, H9 and H12, or H1, H2, H9 and H13, or H1, H2, H11 and H12, or H1, H2, H11 and H13, or H1, H2, H12 and H13, or H1, H5, H6 and H8, or H1, H5, H6 and H9, or H1, H5, H6 and H11, or H1, H5, H6 and H12, or H1, H5, H6 and H13, or H1, H5, H8 and H9, or H1, H5, H8 and H11, or H1, H5, H8 and H12, or H1, H5, H8 and H13, or H1, H5, H9 and H11, or H1, H5, H9 and H12, or H1, H5, H9 and H13, or H1, H5, H11 and H12, or H1, H5, H11 and H13, or H1, H5, H12 and H13, or H1, H6, H8 and H9, or H1, H6, H8 and H11, or H1, H6, H8 and H12, or H1, H6, H8 and H13, or H1, H6, H9 and H11, or H1, H6, H9 and H12, or H1, H6, H9 and H13, or H1, H6, H11 and H12, or H1, H6, H11 and H13, or H1, H6, H12 and H13, or H1, H8, H9 and H11, or H1, H8, H9 and H12, or H1, H8, H9 and H13, or H1, H8, H11 and H12, or H1, H8, H11 and H13, or H1, H8, H12 and H13, or H1, H9, H11 and H12, or H1, H9, H11 and H13, or H1, H9, H12 and H13, or H1, H11, H12 and H13, or H2, H5, H6 and H8, or H2, H5, H6 and H9, or H2, H5, H6 and H11, or H2, H5, H6 and H12, or H2, H5, H6 and H23, or H2, H5, H8 and H9, or H2, H5, H8 and H11, or H2, H5, H8 and H12, or H2, H5, H8 and H13, or H2, H5, H9 and H11, or H2, H5, H9 and H12, or H2, H5, H9 and H13, or H2, H5, H11 and H12, or H2, H5, H11 and H13, or H2, H5, H12 and H13, or H2, H6, H8 and H9, or H2, H6, H8 and H11, or H2, H6, H8 and H12, or H2, H6, H8 and H13, or H2, H6, H9 and H11, or H2, H6, H9 and H12, or H2, H6, H9 and H13, or H2, H6, H11 and H12, or H2, H6, H11 and H13, or H2, H6, H12 and H13, or H2, H8, H9 and H11, or H2, H8, H9 and H12, or H2, H8, H9 and H13, or H2, H8, H11 and H12, or H2, H8, H11 and H13, or H2, H8, H12 and H13, or H2, H9, H11 and H12, or H2, H9, H11 and H13, or H2, H9, H12 and H13, or H2, H11, H12 and H13, or H5, H6, H8 and H9, or H5, H6, H8 and H11, or H5, H6, H8 and H12, or H5, H6, H8 and H13, or H5, H6, H9 and H11, or H5, H6, H9 and H12, or H5, H6, H9 and H13, or H5, H6, H11 and H12, or H5, H6, H11 and H13, or H5, H6, H12 and H13, or H5, H8, H9 and H11, or H5, H8, H9 and H12, or H5, H8, H9 and H13, or H5, H8, H11 and H12, or H5, H8, H11 and H13, or H5, H8, H12 and H13, or H5, H9, H11 and H12, or H5, H9, H11 and H13, or H5, H9, H12 and H13, or H5, H11, H12 and H13, or H6, H8, H9 and H11, or H6, H8, H9 and H12, or H6, H8, H9 and H13, or H6, H8, H11 and H12, or H6, H8, H11 and H13, or H6, H8, H12 and H13, or H6, H9, H11 and H12, or H6, H9, H11 and H13, or H6, H9, H12 and H13, or H6, H11, H12 and H13, or H8, H9, H11 and H12, or H8, H9, H11 and H13, or H8, H9, H12 and H13, or H8, H11, H12 and H13, or H9, H11, H12 and H13;

where 4 group 2 subtypes are mentioned, the combination of some embodiments is H3, H4, H7 and H10, or H3, H4, H7 and H14, or H3, H4, H10 and H14, or H3, H7, H10 and H14, or H4, H7, H10 and H14; where 5 group 1 subtypes are mentioned, the combination is H1, H2, H5, H6, and H8; where 5 group 2 subtypes are mentioned, the combination is H3, H4, H7, H10 and H14.

5 group 1 subtypes in some embodiments are H1, H2, H5, H6, and H8; or H1, H2, H5, H6 and H9, or H1, H2, H5, H6 and H11, or H1, H2, H5, H6 and H12, or H1, H2, H5, H6 and H13, or H1, H2, H5, H8 and H9, or H1, H2, H5, H8 and H11, or H1, H2, H5, H8 and H12, or H1, H2, H5, H8 and H13, or H1, H2, H5, H9 and H11, or H1, H2, H5, H9 and H12, or H1, H2, H5, H9 and H13, or H1, H2, H5, H11 and H12, or H1, H2, H5, H11 and H13, or H1, H2, H5, H12 and H13, or H1, H2, H6, H8 and H9, or H1, H2, H6, H8 and H11, or H1, H2, H6, H8 and H12, or H1, H2, H6, H8 and H13, or H1, H2, H6, H9 and H11, or H1, H2, H6, H9 and H12, or H1, H2, H6, H9 and H13, or H1, H2, H6, H11 and H12, or H1, H2, H6, H11 and H13, or H1, H2, H6, H12 and H13, or H1, H2, H8, H9 and H11, or H1, H2, H8, H9 and H12, or H1, H2, H8, H9 and H13, or H1, H2, H8, H11 and H12, or H1, H2, H8, H11 and H13, or H1, H2, H9, H11 and H12, or H1, H2, H9, H11 and H13, or H1, H2, H9, H12 and H13, or H1, H2, H11, H12 and H13, or H1, H5, H6, H8 and H9 or H1, H5, H6, H8 and H11, or H1, H5, H6, H8 and H12, or H1, H5, H6, H8 and H13, or H1, H5, H6, H9 and H11, or H1, H5, H6, H9 and H12, or H1, H5, H6, H9 and H13, or H1, H5, H6, H11 and H12, or H1, H5, H6, H11 and H13, or H1, H5, H6, H12 and H13, or H1, H5, H8, H9 and H11, or H1, H5, H8, H9 and H12, or H1, H5, H8, H9 and H13, or H1, H5, H8, H11 and H12, or H1, H5, H8, H11 and H13, or H1, H5, H8, H12 and H13, or H1, H5, H9, H11 and H12, or H1, H5, H9, H11 and H13, or H1, H5, H9, H12 and H13, or H1, H5, H11, H12 and H13, or H1, H8, H9, H11 and H12, or H1, H8, H9, H11 and H13, or H1, H8, H9, H12 and H13, or H1, H8, H11, H12 and H13;
5 group 2 subtypes in some embodiments are H3, H4, H7, H10 and H14, or H3, H4, H7, H10 and H15, or H3, H4, H7, H14 and H15, or H3, H4, H10, H14 and H15, or H3, H7, H10, H14 and H15, or H4, H7, H10, H14 and H15;
6 group 1 subtypes in some embodiments are H1, H2, H5, H6, H8 and H9; or H1, H2, H5, H6, H8 and H11; or H1, H2, H5, H6, H8 and H12; or H1, H2, H5, H6, H8 and H13; or H1, H2, H5, H6, H9 and H11; or H1, H2, H5, H6, H9 and H12; or H1, H2, H5, H6, H9 and H13; or H1, H2, H5, H6, H11 and H12; or H1, H2, H5, H6, H11 and H13; or H1, H2, H5, H6, H12 and H13; or H1, H2, H5, H8, H9 and H11; or H1, H2, H5, H8, H9 and H12; or H1, H2, H5, H8, H9 and H13; or H1, H2, H5, H8, H11 and H12; or H1, H2, H5, H8, H11 and H13; or H1, H2, H5, H8, H12 and H13; or H1, H2, H5, H9, H11 and H12; or H1, H2, H5, H9, H11 and H13; or H1, H2, H5, H9, H12 and H13; or H1, H2, H5, H11, H12 and H13; or H1, H2, H6, H8, H9 and H11; or H1, H2, H6, H8, H9 and H12; or H1, H2, H6, H8, H9 and H13; or H1, H2, H6, H8, H11 and H12; or H1, H2, H6, H8, H11 and H13; or H1, H2, H6, H8, H12 and H13; or H1, H2, H6, H9, H11 and H12; or H1, H2, H6, H9, H11 and H13; or H1, H2, H6, H9, H12 and H13; or H1, H2, H6, H11, H12 and H13; or H1, H2, H8, H9, H11 and H12; or H1, H2, H8, H9, H11 and H13; or H1, H2, H8, H9, H12 and H13; or H1, H2, H8, H11, H12 and H13; or H1, H2, H9, H11, H12 and H13; or H1, H5, H6, H8, H9 and H11; or H1, H5, H6, H8, H9 and H12; or H1, H5, H6, H8, H9 and H13; or H1, H5, H6, H8, H11 and H12; or H1, H5, H6, H8, H11 and H13; or H1, H5, H6, H8, H12 and H13; or H1, H5, H6, H9, H11 and H12; or H1, H5, H6, H9, H11 and H13; or H1, H5, H6, H9, H12 and H13; or H1, H5, H6, H11, H12 and H13; or H1, H5, H8, H9, H11 and H12; or H1, H5, H8, H9, H11 and H13; or H1, H5, H8, H9, H12 and H13; or H1, H5, H8, H11, H12 and H13; or H1, H5, H9, H11, H12 and H13; or H1, H6, H8, H9, H11 and H13; or H1, H6, H8, H9, H12 and H13; or H1, H6, H8, H11, H12 and H13; or H1, H6, H9, H11, H12 and H13; or H1, H8, H9, H11, H12 and H13.

7 group 1 subtypes in some embodiments are H1, H2, H5, H6, H8, H9 and H11, or H1, H2, H5, H6, H8, H9 and H12, or H1, H2, H5, H6, H8, H9 and H13, or H1, H2, H5, H6, H8, H11 and H12, or H1, H2, H5, H6, H8, H11 and H13, or H1, H2, H5, H6, H9, H11 and H12, or H1, H2, H5, H6, H9, H11 and H13, or H1, H2, H5, H6, H9, H12 and H13, or H1, H2, H5, H6, H11, H12 and H13, or H1, H2, H5, H8, H9, H11 and H13, or H1, H2, H5, H8, H9, H12 and H13, or H1, H2, H5, H8, H11, H12 and H13, or H1, H2, H5, H9, H11, H12 and H13, or H1, H2, H6, H8, H9, H11 and H13, or H1, H2, H6, H8, H9, H11 and H12, or H1, H2, H6, H8, H11, H12 and H13, or H1, H2, H6, H9, H11, H12 and H13, or H1, H2, H8, H9, H11, H12 and H13, H1, H5, H6, H8, H9, H11 and H13, or H1, H5, H6, H8, H9, H12 and H13, or H1, H5, H6, H8, H11, H12 and H13, or H1, H5, H6, H9, H11, H12 and H13, or H1, H5, H8, H9, H11, H12 and H13, or H1, H6, H8, H9, H11, H12 and H13.

8 group 1 subtypes in some embodiments are H1, H2, H5, H6, H8, H9, H11 and H12, or H1, H2, H5, H6, H8, H9, H11 and H13, or H1, H2, H5, H6, H8, H9, H12 and H13, or H1, H2, H5, H6, H8, H11, H12 and H13, or H1, H2, H5, H6, H9, H11, H12 and H13, or H1, H2, H5, H8, H9, H11, H12 and H13, or H1, H5, H5, H8, H9, H11, H12 and H13, or H2, H5, H6, H8, H9, H11, H12 and H13.

9 group 1 subtypes in some embodiments are H1, H2, H5, H6, H8, H9, H11, H12 and H13.

According to some embodiments, the nucleic acid sequences from which the library members are prepared, are obtained from B cells isolated from an individual—for most purposes a human being—previously exposed to influenza hemagglutinin. A library of such nucleic acid sequences may be constructed using the antibody encoding genes isolated from these B cells. The antibody genes from individual B cells can be obtained by amplification of their coding region in a PCR reaction, and the amplified antibody genes can be subsequently cloned into a suitable vector, such as phagemid for phage display.

According to some embodiments, the panning antigen comprises a hemagglutinin stem region polypeptide sequence of non-human influenza A virus isolate. In one embodiment, the hemagglutinin stem region polypeptide sequence originates from an avian H7 strain. In one embodiment, this is the strain H7N7. HA from isolate A/FPV/Bratislava/1979 (H7N7), a highly pathogenic avian influenza (HPAI) strain belonging to group 2, is one particular example.

The objective of most embodiments of the present invention will be the provision of therapy, prevention or diagnosis for human patients. For this purpose, the library may be biased for recognition of HA sequences naturally occurring in human patients. Hence, using B cell immunoglobulin encoding sequences from human patients with prior exposure to influenza HA as point of departure for the library, is of advantage in such cases.

Human patients may have been exposed to influenza HA by infection or vaccination. In both cases, the HA subtype the patient had been exposed to, is likely to be a subtype typically occurring in humans. If the specific objective of finding a cross-subtype specific antibody is for therapy or prevention of a specific animal species, a library may be built from B cell sequences from such animals.

Using a non-human influenza A isolate additionally confers the advantage of providing an antigen, the subtype-specific epitopes of which are unlikely to be recognized by a significant portion of the B cell repertoire used to build the library. Especially in embodiments where the dampening of the apical region of the panning antigen is achieved by steric hindrance, as is preferred in the context of the present invention, using an apical region from a subtype that the individual who provided the library was previously not exposed to, brings protection against eventual "leakage" of the dampening.

According to yet another embodiment, the panning antigen comprises a hemagglutinin stem region polypeptide sequence of a human H2 influenza virus isolate, preferably from the strain H2N2. A most preferred panning antigen is derived from isolate A/Japan/305/1957(H2N2) or JP57, a human isolate belonging to phylogenetic group 1. Since H2 expressing viruses only circulated between 1957 and 1967, all individuals born after 1968 are very unlikely to have been exposed to this subtype and are therefore immunologically naïve to it.

Tethering of the apical region to a globular structure or a surface exposes the stem region, which contains the region conferring multi-strain specificity on the selected antibodies or polypeptides, while shielding strain-specific regions contained in the apical region. Access to the apical region is thus restrained by steric hindrance.

Thus, according to another embodiment, the panning antigen comprises a hemagglutinin apical polypeptide sequence attached at residue 150 to 170 to a globular or surface structure by a tether of less than 4 nm.

Such tether may be a thio-reactive linker comprising an additional functional group that can be specifically attached to a globular or surface structure. An exemplary functional group is biotin. The thio-reactive linker may be covalently attached to the side chain of a cystein residue comprised in the apical region, preferably a cysteine located between residue 150 and 170 of the hemagglutinin apical polypeptide sequence described in the preceding paragraph. Optionally, a cystein residue may be introduced at residues 150 to 170 by suitable methods such as mutagenesis. A thio-reactive linker in the sense of the invention refers to a compound capable of forming a covalent bond to the thiol group of a cystein residue side chain. One example is the Biotin Maleimide reagent available from Pierce or Vector Laboratories (USA).

According to some embodiments, the extracellular portion of the HA proteins (i.e. all of HA1 and aa 1 to 184 of HA2) are mutated to contain a cysteine residue between residues 150 to 170 of HA1, depending on the isolate, to achieve antigen orientation and silencing of the strain-specific epitopes. This location, and the lack of other reduction sensitive and solvent accessible cysteine residues ensures that thio-reactive chemistry can be used to covalently attach moieties to a very apical location of the HA protein. Possible ligands to be attached to the HA protein encompass either bulky but antigenically inert moieties that impair antibody access to the strain-specific apical epitopes. In particular, the apical thioreactive groups can also be used to covalently tether the protein in an upside-down orientation to solid surfaces. Such tethering does not only block access of antibodies to the apical epitopes but also ensures a prominent exposure of the HA stem with its conserved epitopes.

Such globular structure may be a polypeptide that can specifically recognize and bind a tether described in the preceding paragraphs. A preferred globular structure is avidin or streptavidin. Another preferred globular structure is a second HA molecule attached also through a linker bound to its apical region.

Alternatively, the tether according to the above aspect may comprise any suitable functional group such as an affinity tag. Likewise, the globular structure may be a corresponding polypeptide that specifically binds the affinity tag. Examples for affinity tags and corresponding polypeptides include, without being restricted to, glutathione and glutathione S-transferase, maltose and maltose binding protein or carbohydrate and lectin such as Concanavalin A.

A surface structure may be large structure such as a well or a bead covered with the polypeptide described above, preferably avidin or streptavidin.

In one embodiment the binding step and the washing step are repeated 2 to 25 times. Where no mutagenesis or recombination steps are included, and hence the best binders are merely selected from a pool of potential binders, such as is the case with B-cell immunoglobulin libraries generated from a patient previously exposed to antigen by infection or vaccination or both, the steps are repeated only 2, 3, 4, 5 or 6 times.

In one embodiment the polypeptide reactive to influenza A hemagglutinin is a gamma immunoglobulin.

According to a second aspect of the invention, an isolated polypeptide capable of neutralizing influenza A virus from at least 5 subtypes, at least one of which is a group 1 subtype and at least one of which is a group 2 subtype, is provided. Such polypeptide can be obtained by the method of the invention described above.

In some embodiments, at least two neutralized subtypes are group 1 subtypes and at least two are group 2 subtypes. Such polypeptide can be obtained by a method according to the above aspect of the invention.

In some embodiments, the polypeptide neutralizes HA of the subtypes 1, 2 and 3.

In one embodiment, the polypeptide neutralizes HA of the subtypes 1, 2, 5 and 3. In one embodiment, the polypeptide neutralizes HA of the subtypes 1, 2, 5 and 4. In one embodiment, the polypeptide neutralizes HA of the subtypes 1, 2, 3 and 4. In one embodiment, the polypeptide neutralizes HA of the subtypes 1, 2, 3 and 7. In one embodiment, the polypeptide neutralizes HA of the subtypes 1, 2, 3, 4 and 7.

In some embodiments, the polypeptide neutralizes HA of
2 group 1 subtypes and 5 or 6 group 2 subtypes, or
3 group 1 subtypes and 5 or 6 group 2 subtypes, or
4 group 1 subtypes and 2, 3, 4, 5 or 6 group 2 subtypes, or
5 group 1 subtypes and 2, 3, 4, 5 or 6 group 2 subtypes, or
6 group 1 subtypes and 2, 3, 4, 5 or 6 group 2 subtypes, or
7 group 1 subtypes and 2, 3, 4, 5 or 6 group 2 subtypes, or
8 group 1 subtypes and 2, 3, 4, 5 or 6 group 2 subtypes, or
9 group 1 subtypes, and 2, 3, 4, 5 or 6 group 2 subtypes.

For embodiments, where 2 group 1 subtypes are mentioned above, a preferred combination is H1 and H2; or H1 and H5; or H1 and H6; or H1 and H8; or H1 and H9; or H1 and H11; or H1 and H12; or H1 and H13; or H2 and H5; or H2 and H6; or H2 and H8; or H2 and H9; or H2 and H11; or H2 and H12; or H2 and H13; or H5 and H6; or H5 and H8; or H5 and H9; or H5 and H11; or H5 and H12; or H5 and H13; or H6 and H8; or H6 and H9; or H6 and H11; or H6 and H12; or H6 and H13; or H8 and H9; or H8 and H11; or H8 and H12; or H8 and H13; or H9 and H11; or H9 and H12; or H9 and H13; or H11 and H12; or H11 and H13; or H12 and H13.

Similarly, where 2 group 2 subtypes are mentioned above, a preferred combination is H3 and H4, or H3 and H7, or H3 and H10, or H3 and H14, or H3 and H15, or H4 and H7, or H4 and H10, or H4 and H14, or H4 and H15, or H7 and H10, or H7 and H14, or H7 and H15, or H10 and H14, or H10 and H15, or H14 and H15;

where 3 group 1 subtypes are mentioned, a preferred combination is H1, H2 and H5; or H1, H2 and H6; or H1, H2 and H8; or H1, H2 and H9; or H1, H2 and H11; or H1, H2 and H12; or H1, H2 and H13; or H1, H5 and H8; or H1, H5 and H9; or H1, H5 and H11; or H1, H5 and H12; or H1, H5 and H13; or H1, H8 and H9; or H1, H8 and H11; or H1, H8 and H12; or H1, H8 and H13; or H1, H9 and H11; or H1, H9 and H12; or H1, H9 and H13; or H1, H11 and H12; or H1, H11 and H13; or H1, H12 and H13; or H2, H5 and H6; or H2, H5 and H8; or H2, H5 and H9; or H2, H5 and H11; or H2, H5 and H12; or H2, H5 and H12; or H2, H5 and H13; or H2, H6 and H8; or H2, H6 and H9; or H2, H6 and H11; or H2, H6 and H12; or H2, H6 and H13; or H2, H8 and H9; or H2, H8 and H11; or H2, H8 and H12; or H2, H8 and H13; or H2, H9 and H11; or H2, H9 and H12; or H2, H9 and H13; or H2, H11 and H12; or H2, H11 and H13; or H2, H12 and H13; or H5, H6 and H8; or H5, H6 and H9; or H5, H6 and H11; or H5, H6 and H12; or H5, H6 and H13; or H5, H8 and H9; or H5, H8 and H11; or H5, H8 and H12; or H5, H8 and H13; or H5, H9 and H11; or H5, H9 and H12; or H5, H9 and H13; or H5, H11 and H12; or H5, H11 and H13; or H5, H12 and H13; or H6, H8 and H9; or H6, H8 and H11; or H6, H8 and H12; or H6, H8 and H13; or H6, H9 and H11; or H6, H9 and H12; or H6, H9 and H13; or H6, H11 and H12; or H6, H11 and H13; or H6, H12 and H13; or H8, H9 and H11; or H8, H9 and H12; or H8, H9 and H13; or H8, H11 and H12; or H8, H11 and H13; or H8, H12 and H13; or H9, H11 and H12; or H9, H11 and H13; or H9, H12 and H13; or H11, H12 and H13;

where 3 group 2 subtypes are mentioned, the combinations H3, H4 and H7; or H3, H4 and H10; or H3, H4 and H14; or H3, H4 and H15; or H3, H7 and H10; or H3, H7 and H14; or H3, H7 and H15; or H3, H10 and H14; or H3, H10 and H15; or H3, H14 and H15; or H4, H7 and H10; or H4, H7 and H14; or H4, H7 and H15; or H7, H10 and H14; or H7, H10 and H15; or H10, H14 and H15 are preferred;

where 4 group 1 subtypes are mentioned, the combinations H1, H2, H5 and H6, or H1, H2, H5 and H8, or H1, H2, H5 and H9, or H1, H2, H5 and H11, or H1, H2, H5 and H12, or H1, H2, H5 and H13, or H1, H2, H6 and H8, or H1, H2, H6 and H9, or H1, H2, H6 and H11, or H1, H2, H6 and H12, or H1, H2, H6 and H13, or H1, H2, H8 and H9, or H1, H2, H8 and H11, or H1, H2, H8 and H12, or H1, H2, H8 and H13, or H1, H2, H9 and H11, or H1, H2, H9 and H12, or H1, H2, H9 and H13, or H1, H2, H11 and H12, or H1, H2, H11 and H13, or H1, H2, H12 and H13, or H1, H5, H6 and H8, or H1, H5, H6 and H9, or H1, H5, H6 and H11, or H1, H5, H6 and H12, or H1, H5, H6 and H13, or H1, H5, H8 and H9, or H1, H5, H8 and H11, or H1, H5, H8 and H12, or H1, H5, H8 and H13, or H1, H5, H9 and H11, or H1, H5, H9 and H12, or H1, H5, H9 and H13, or H1, H5, H11 and H12, or H1, H5, H11 and H13, or H1, H5, H12 and H13, or H1, H6, H8 and H9, or H1, H6, H8 and H11, or H1, H6, H8 and H12, or H1, H6, H8 and H13, or H1, H6, H9 and H11, or H1, H6, H9 and H12, or H1, H6, H9 and H13, or H1, H6, H11 and H12, or H1, H6, H11 and H13, or H1, H6, H12 and H13, or H1, H8, H9 and H11, or H1, H8, H9 and H12, or H1, H8, H9 and H13, or H1, H8, H11 and H12, or H1, H8, H11 and H13, or H1, H8, H12 and H13, or H1, H9, H11 and H12, or H1, H9, H11 and H13, or H1, H9, H12 and H13, or H1, H11, H12 and H13, or H2, H5, H6 and H8, or H2, H5, H6 and H9, or H2, H5, H6 and H11, or H2, H5, H6 and H12, or H2, H5, H6 and H23, or H2, H5, H8 and H9, or H2, H5, H8 and H11, or H2, H5, H8 and H12, or H2, H5, H8 and H13, or H2, H5, H9 and H11, or H2, H5, H9 and H12, or H2, H5, H9 and H13, or H2, H5, H11 and H12, or H2, H5, H11 and H13, or H2, H5, H12 and H13, or H2, H6, H8 and H9, or H2, H6, H8 and H11, or H2, H6, H8 and H12, or H2, H6, H8 and H13, or H2, H6, H9 and H11, or H2, H6, H9 and H12, or H2, H6, H9 and H13, or H2, H6, H11 and H12, or H2, H6, H11 and H13, or H2, H6, H12 and H13, or H2, H8, H9 and H11, or H2, H8, H9 and H12, or H2, H8, H9 and H13, or H2, H8, H11 and H12, or H2, H8, H11 and H13, or H2, H8, H12 and H13, or H2, H9, H11 and H12, or H2, H9, H11 and H13, or H2, H9, H12 and H13, or H2, H11, H12 and H13, or H5, H6, H8 and H9, or H5, H6, H8 and H11, or H5, H6, H8 and H12, or H5, H6, H8 and H13, or H5, H6, H9 and H11, or H5, H6, H9 and H12, or H5, H6, H9 and H13, or H5, H6, H11 and H12, or H5, H6, H11 and H13, or H5, H6, H12 and H13, or H5, H8, H9 and H11, or H5, H8, H9 and H12, or H5, H8, H9 and H13, or H5, H8, H11 and H12, or H5, H8, H11 and H13, or H5, H8, H12 and H13, or H5, H9, H11 and H12, or H5, H9, H11 and H13, or H5, H9, H12 and H13, or H5, H11, H12 and H13, or H6, H8, H9 and H11, or H6, H8, H9 and H12, or H6, H8, H9 and H13, or H6, H8, H11 and H12, or H6, H8, H11 and H13, or H6, H8, H12 and H13, or H6, H9, H11 and H12, or H6, H9, H11 and H13, or H6, H9, H12 and H13, or H6, H11, H12 and H13, or H8, H9, H11 and H12, or H8, H9, H11 and H13, or H8, H9, H12 and H13, or H8, H11, H12 and H13, or H9, H11, H12 and H13 are preferred;

where 4 group 2 subtypes are mentioned, the combination is H3, H4, H7 and H10; or H3, H4, H7 and H14; or H3, H4, H7 and H15; or H3, H7, H10 and H14; or H3, H7, H10 and H15; or H3, H10, H14 and H15; or H4, H7, H10 and H14; or H4, H7, H10 and H15; or H4, H10, H14 and H15; or H7, H10, H14 and H15;

where 5 group 1 subtypes are mentioned, a preferred combination is H1, H2, H5, H6, and H8; or H1, H2, H5, H6 and H9, or H1, H2, H5, H6 and H11, or H1, H2, H5, H6 and H12, or H1, H2, H5, H6 and H13, or H1, H2, H5, H8 and H9, or H1, H2, H5, H8 and H11, or H1, H2, H5, H8 and H12, or H1, H2, H5, H8 and H13, or H1, H2, H5, H9 and H11, or H1, H2, H5, H9 and H12, or H1, H2, H5, H9 and H13, or H1, H2, H5, H11 and H12, or H1, H2, H5, H11 and H13, or H1, H2, H5, H12 and H13, or H1, H2, H6, H8 and H9, or H1, H2, H6, H8 and H11, or H1, H2, H6, H8 and H12, or H1, H2, H6, H8 and H13, or H1, H2, H6, H9 and H11, or H1, H2, H6, H9 and H12, or H1, H2, H6, H9 and H13, or H1, H2, H6, H11 and H12, or H1, H2, H6, H11 and H13, or H1, H2, H6, H12 and H13, or H1, H2, H8, H9 and H11, or H1, H2, H8, H9 and H12, or H1, H2, H8, H9 and H13, or H1, H2, H8, H11 and H12, or H1, H2, H8, H11 and H13, or H1, H2, H8, H12 and H13, or H1, H2, H9, H11 and H12, or H1, H2, H9, H11 and H13, or H1, H2, H9, H12 and H13, or H1, H2, H11, H12 and H13, or H1, H5, H6, H8 and H9 or H1, H5, H6, H8 and H11, or H1, H5, H6, H8 and H12, or H1, H5, H6, H8 and H13, or H1, H5, H6, H9 and H11, or H1, H5, H6, H9 and H12, or H1, H5, H6, H9 and H13, or H1, H5, H6, H11 and H12, or H1, H5, H6, H11 and H13, or H1, H5, H6, H12 and H13, or H1, H5, H8, H9 and H11, or H1, H5, H8, H9 and H12, or H1, H5, H8, H9 and H13, or H1, H5, H8, H11 and H12, or H1, H5, H8, H11 and H13, or H1, H5, H8, H12 and H13, or H1, H5, H9, H11 and H12, or H1, H5, H9, H11 and H13, or H1, H5, H9, H12 and H13, or H1, H5, H11, H12 and H13, or H1, H8, H9, H11 and H12, or H1, H8, H9, H11 and H13, or H1, H8, H9, H12 and H13, or H1, H8, H11, H12 and H13.

Where 5 group 2 subtypes are mentioned, a preferred combination is H3, H4, H7, H10 and H14, or H3, H4, H7, H10 and H15, or H3, H4, H7, H14 and H15, or H3, H4, H10, H14 and H15, or H3, H7, H10, H14 and H15, or H4, H7, H10, H14 and H15.

where 6 group 1 subtypes are mentioned, a preferred combination is H1, H2, H5, H6, H8 and H9; or H1, H2, H5, H6, H8 and H11; or H1, H2, H5, H6, H8 and H12; or H1, H2, H5, H6, H8 and H13; or H1, H2, H5, H6, H9 and H11; or H1, H2, H5, H6, H9 and H12; or H1, H2, H5, H6, H9 and H13; or H1, H2, H5, H6, H11 and H12; or H1, H2, H5, H6, H11 and H13; or H1, H2, H5, H6, H12 and H13; or H1, H2, H5, H8, H9 and H11; or H1, H2, H5, H8, H9 and H12; or H1, H2, H5, H8, H9 and H13; or H1, H2, H5, H8, H11 and H12; or H1, H2, H5, H8, H11 and H13; or H1, H2, H5, H8, H12 and H13; or H1, H2, H5, H9, H11 and H12; or H1, H2, H5, H9, H11 and H13; or H1, H2, H5, H9, H12 and H13; or H1, H2, H5, H11, H12 and H13; or H1, H2, H6, H8, H9 and H11; or H1, H2, H6, H8, H9 and H12; or H1, H2, H6, H8, H9 and H13; or H1, H2, H6, H8, H11 and H12; or H1, H2, H6, H8, H11 and H13; or H1, H2, H6, H8, H12 and H13; or H1, H2, H6, H9, H11 and H12; or H1, H2, H6, H9, H11 and H13; or H1, H2, H6, H9, H12 and H13; or H1, H2, H6, H11, H12 and H13; or H1, H2, H8, H9, H11 and H12; or H1, H2, H8, H9, H11 and H13; or H1, H2, H8, H9, H12 and H13; or H1, H2, H8, H11, H12 and H13; or H1, H2, H9, H11, H12 and H13; or H1, H5, H6, H8, H9 and H11; or H1, H5, H6, H8, H9 and H12; or H1, H5, H6, H8, H9 and H13; or H1, H5, H6, H8, H11 and H12; or H1, H5, H6, H8, H11 and H13; or H1, H5, H6, H8, H12 and H13; or H1, H5, H6, H9, H11 and H12; or H1, H5, H6, H9, H11 and H13; or H1, H5, H6, H9, H12 and H13; or H1, H5, H6, H11, H12 and H13; or H1, H5, H8, H9, H11 and H12; or H1, H5, H8, H9, H11 and H13; or H1, H5, H8, H9, H12 and H13; or H1, H5, H8, H11, H12 and H13; or H1, H5, H9, H11, H12 and H13; or H1, H5, H8, H9, H11 and H12; or H1, H5, H8, H9, H11 and H13; or H1, H5, H8, H9, H12 and H13; or H1, H5, H8, H11, H12 and H13; or H1, H5, H9, H11, H12 and H13; or H1, H6, H8, H9, H11 and H13; or H1, H6, H8, H9, H12 and H13; or H1, H6, H8, H11, H12 and H13; or H1, H6, H9, H11, H12 and H13; or H1, H8, H9, H11, H12 and H13.

7 group 1 subtypes in some embodiments are H1, H2, H5, H6, H8, H9 and H11, or H1, H2, H5, H6, H8, H9 and H12, or H1, H2, H5, H6, H8, H9 and H13, or H1, H2, H5, H6, H8, H11 and H12, or H1, H2, H5, H6, H8, H11 and H13, or H1, H2, H5, H6, H9, H11 and H12, or H1, H2, H5, H6, H9, H11 and H13, or H1, H2, H5, H6, H9, H12 and H13, or H1, H2, H5, H6, H11, H12 and H13, or H1, H2, H5, H8, H9, H11 and H13, or H1, H2, H5, H8, H9, H12 and H13, or H1, H2, H5, H8, H11, H12 and H13, or H1, H2, H5, H9, H11, H12 and H13, or H1, H2, H6, H8, H9, H11 and H13, or H1, H2, H6, H8, H9, H12 and H13, or H1, H2, H6, H8, H11, H12 and H13, or H1, H2, H6, H9, H11, H12 and H13, or H1, H2, H8, H9, H11, H12 and H13, H1, H5, H6, H8, H9, H11 and H13, or H1, H5, H6, H8, H9, H12 and H13, or H1, H5, H6, H8, H11, H12 and H13, or H1, H5, H6, H9, H11, H12 and H13, or H1, H5, H8, H9, H11, H12 and H13, or H1, H6, H8, H9, H11, H12 and H13.

8 group 1 subtypes in some embodiments are H1, H2, H5, H6, H8, H9, H11 and H12, or H1, H2, H5, H6, H8, H9, H11 and H13, or H1, H2, H5, H6, H8, H9, H12 and H13, or H1, H2, H5, H6, H8, H11, H12 and H13, or H1, H2, H5, H6, H9, H11, H12 and H13, or H1, H2, H5, H8, H9, H11, H12 and H13, or H1, H5, H5, H8, H9, H11, H12 and H13, or H2, H5, H6, H8, H9, H11, H12 and H13.

9 group 1 subtypes in some embodiments are H1, H2, H5, H6, H8, H9, H11, H12 and H13.

Such polypeptide according to the second aspect of the invention may be an antibody or an antibody fragment. An antibody fragment may be a Fab domain or a Fv domain of an antibody, a single-chain antibody fragment, which is a fusion protein consisting of the variable regions of light and heavy chains of an antibody connected by a peptide linker. It may also be a single domain antibody, consisting of an isolated variable domain from a heavy or light chain. Additionally, a polypeptide according to the second aspect of the invention may also be a heavy-chain antibody consisting of only heavy chains such as antibodies found in camelids.

According to one embodiment, the polypeptide is a gamma immunoglobulin. In general, immunoglobulins or fragments thereof, such as an antigen-binding fragment Fab, a variable fragment Fv or a single-chain variable fragment scFv are well suited to practice the invention, particularly gamma immunoglobulin molecules comprising at least part of the constant domain, as a significant part of the physiological mechanism by which the antibody confers protection to a patient, is mediated through the constant domain.

In one embodiment, the polypeptide comprises a polypeptide sequence encode by variable region germline IGHV1-69.

In some embodiments, the polypeptide is capable of neutralizing virus of at least five subtypes. In one embodiment, the polypeptide is capable of neutralizing virus of both phylogenetic groups. This means that at least five subtypes are subtypes of both group 1 and group 2.

In one embodiment, the polypeptide according to the second aspect of the invention neutralizes virus of the subtypes H1N1, H2N2, H5N3, H6N1, and H8N4 (belonging to group 1), and H3N2, H4N6, H7N7, H10N7, and H14N5 (belonging to group 2), in vitro.

A polypeptide is capable of neutralizing influenza A virus in the sense of the invention, if the half maximal effective concentration (EC50 value) of the polypeptide is 10 µg/ml or smaller. Preferred polypeptides are antibodies with an EC50 value of 5 or smaller.

The neutralization assays are performed as follows: Cells were seeded at $2.0 \times 10^4$ cells per well into 96-well plates the day before the assay. Antibody of interest was titrated 1:2 in triplicates starting at 300 µg/ml in infection medium (DMEM with 0.2% BSA). At the day of the assay, virus was diluted to obtain an moi of 3 in a volume of 40 µl. 20 µl of the antibody dilution was mixed with 40 µl of the virus dilution and incubated at 37°/$CO_2$ for 2 hours. The cell/virus mixture was then added to PBS-washed cells and virus attachment was allowed to proceed for 1 h before the antibody/virus mixture was aspirated and cells washed. Infection medium was added, and cells were incubated at 37°/$CO_2$ for 5-6 hours. For detection of productive infections, cells were fixed with methanol and stained with a fluorescein-labelled monoclonal antibody against the viral NP protein (ATCC HB-65, or H16-L10-4R5 (Yewdell et al. (1981), J Immunol 126(5): 1814-1819.)). Cells were counterstained with DAPI and fluorescence was read at 25 distinct points of each well. The average of the fluorescence values was taken for each well, and plotted as average of the 3 replicate values with the standard deviations.

In one embodiment, a polypeptide is provided that is capable of binding to hemagglutinin of the subtypes:

H1, H2 and H12 (belonging to group 1), and

H3 and H7 (belonging to group 2).

A polypeptide is capable of binding to hemagglutinin of any subtype described above in the sense of the invention, if the disassociation constant is $10^{-7}$ mol/l or smaller. Preferred polypeptides have a disassociation constant of $10^{-8}$ mol/l According to another aspect of the invention, a polypeptide is provided comprising a sequence encoded by a nucleotide sequence selected from the group comprised of Seq. ID 01 (mAB1.12 heavy chain), Seq. ID 02 (mAB 1.12 light chain), Seq. ID 03 (mAB 3.1 heavy chain), Seq. ID 04 (mAB 3.1 light chain) or a polypeptide sequence functionally equivalent to a sequence encoded by a nucleotide sequence Seq. ID 01, Seq. ID 02, Seq. ID 03 or Seq. ID 04, with at least 90% sequence identity, preferably more than 95% sequence identity, more preferably more than 97% sequence identity, most preferably 98% or more sequence identity to the polypeptide encoded by Seq. 01, Seq. ID 02, Seq. ID 03 or Seq. ID 04.

In one embodiment, the polypeptide comprises the sequence encoded by SeqID 01 (mAB1.12 heavy chain) and an IgG light chain. The heavy chain of 1.12 was isolated and tested in combination with at least four different families of light chains. All combinations proved to be cross-reactive with Inf A HA molecules from different subtypes. For example, mAb 1.14 and mAb 1.36 expressing the 1.12 heavy chain in combination with a VL-1-40 and VL1-44, respectively, displayed similar overall properties as mAb1.12 expressing a VL1.39 light chain. Both, mAb1.14 and mAb1.36 have been tested for neutralization of a limited number of group 1 isolates, but no obvious differences to mAb1.12 became apparent.

An antibody comprising the sequences encoded by Seq 01 and Seq. ID 02 is one example of this aspect of the invention.

Identity in the context of the present invention is a single quantitative parameter representing the result of a sequence comparison position by position. Methods of sequence comparison are known in the art; the BLAST algorithm available publicly is an example.

A polypeptide comprising a sequence encoded by Seq. ID 01 and Seq. 02 is a particular example of the invention, as is a polypeptide that comprises a sequence encoded by Seq. ID 03 and Seq. ID 04.

According to particular embodiments, a polypeptide according to the second aspect of the invention may be a monomer or a homo- or hetero-oligomer. A hetero dimer comprising a sequence encoded by Seq. ID 01 and Seq. ID 02 or Seq. ID 03 and Seq. ID 04 is preferred.

Also provided is a nucleic acid comprising a coding sequence encoding a polypeptide sequence according to the invention. Similarly, an expression vector such as a plasmid or artificial chromosome, or a host cell comprising such nucleic acid is deemed to fall under the scope of the present invention.

Similarly, a method for the manufacture of a medicament for therapy and prevention of influenza A infection comprising the use of a polypeptide as described as a second aspect of the invention is provided.

According to another aspect of the invention, a polypeptide according to the above aspects of the invention is provided for use in methods for prevention or therapy of influenza A infection.

Therapeutic applications of the inventive polypeptide are especially useful in treating or preventing zoonotic infections or severe infections, particularly in infants and elderly patients, pregnant women or immune compromised individuals (immune-suppressed organ recipients, inherited or acquired immune deficiencies). Post-exposure prophylaxis is of particular value in suspected zoonotic infections or quarantine supporting measures in case of an emerging pandemic. For pre-exposure prophylaxis, transplant recipients at start of immunosuppression after surgery, prematurely born infants, pregnant women and officials or health care workers in case of a pandemic will be preferred recipients.

Also within the scope of the invention is a pharmaceutical composition comprising a polypeptide according to the above described embodiments of the invention, or a nucleic acid encoding such polypeptide, and a pharmaceutically acceptable carrier, for use in a method for therapy or prevention of influenza A infection.

Similarly considered is the use of a polypeptide according to the invention, in a method for manufacturing a medicament for the prevention and therapy of influenza A infection.

According to yet another aspect of the invention, use of a polypeptide of the invention for diagnosis of influenza A infection is provided. The invention according to this aspect particularly allows capturing or enriching viral particles to increase sensitivity of virus detection, or to detect virus independent of the conserved NP or M proteins commonly used in virus detection.

According to another aspect of the invention, a kit or device for diagnosis of influenza comprising a polypeptide according to the invention is provided.

According to yet another aspect of the invention, a vaccine is provided comprising a hemagglutinin having an exposed stem sequence and an apical sequence attached at residue 150 to 170, to a globular or surface structure by a tether of less than 4 nm.

A preferred tether may be thio-reactive linker comprising a biotin moiety as described in the preceding aspects of the invention. The thio-reactive linker may be covalently bound to the side chain of a cystein residue located at residue 150 to 170 of the hemagglutinin described in the preceding paragraph. In one embodiment, the globular structure is avidin or streptavidin. In one embodiment, the globular structure is a second hemagglutinin having an exposed stem sequence, which is attached to the first one by a tether or linker to its apical sequence at residue 150 to 170. Thereby, two hemagglutinin molecules are attached to one another, shielding their respective apical structure while exposing the stems.

Such vaccine may further comprise a pharmaceutically acceptable carrier such as saline buffer, in particular phosphate buffered saline. Additionally, a vaccine according to the above aspect may comprise adjuvants that stimulate the immune system of a subject and increase the response to the administered vaccine.

Adjuvants include, without being restricted to, aluminum salts, organic compounds such squalene, lipopolysaccharides, CpG-oligonucleotides, virosomes or saponins such as QS21, which is a mixture of soluble triterpene glucoside compounds.

According to another aspect of the invention, a vaccine is provided comprising two hemagglutinin polypeptides, each having a stem sequence and an apical sequence, wherein one apical sequence is attached to another apical sequence at residue 150 to 170 by a tether of less than 4 nm.

Preferably, the hemagglutinin polypeptides of such vaccine are connected by thio-reactive linkers via biotin moieties linked to avidin or streptavidin, whereby at least one thio-reactive linker of each of two polypeptides binds the same avidin or streptavidin molecule.

According to another aspect of the invention, a vaccine according to any of the above aspects of the invention is provided for prevention of influenza A infection.

In summary, the advantages of the panning antigen used herein are based on a combination of three considerations for its design. Firstly, the use of a non-human hemagglutinin—or a HA without recent occurrence in humans—as a scaffold compensates for a potential leakiness of the epitope dampening: There are no pre-existing antibodies against the dominant epitopes of non-human HAs. Likewise, if the antigen were to be used for immunization, a primary response would have to be mounted against the non-human immunodominant epitopes while the response against the conserved shared epitope would be swift memory responses. Secondly, steric hindrance prevents access to the strain-specific apical epitopes. Thirdly, the antigen is presented in an oriented and organized fashion.

Wherever the invention is illustrated above by mention of embodiments, it is to be understood that embodiments illustrating certain features of the invention, such as for example a specificity for certain group 1 or group 2 subtypes, may be combined with any other embodiment highlighting a different feature.

The invention is further illustrated by the following Figures and Examples, from which further embodiments and advantages may be drawn.

SHORT DESCRIPTION OF THE FIGURES

Figure 1:
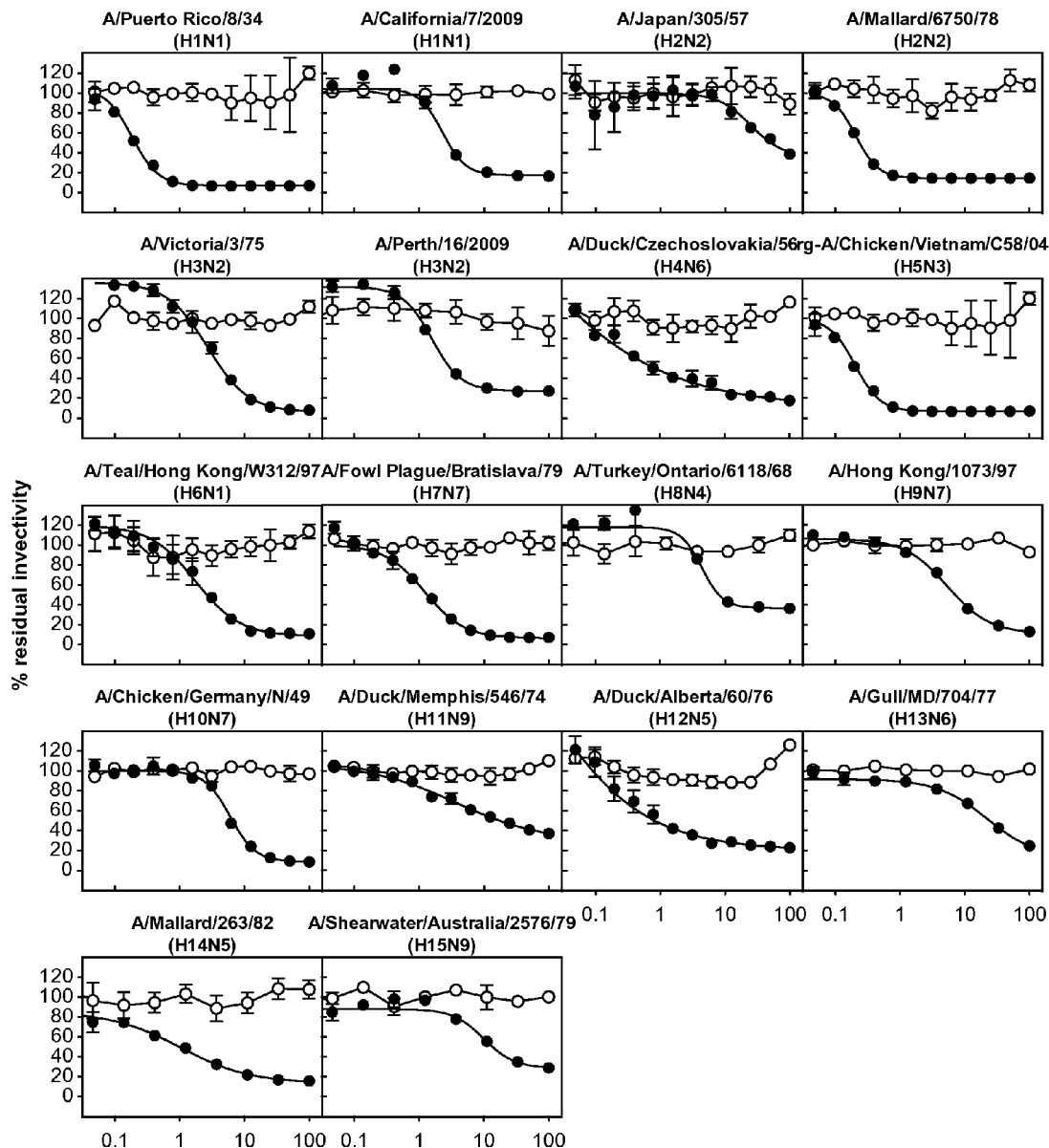
FIG. 1 shows the neutralization of different HA subtypes by mAB 1.12 Fab (filled triangles); mAb 1.12 IgG (filled squares); control Fab fragment and mAB (empty forms), virus only (asterix); cells only (stars).
Figure 2:
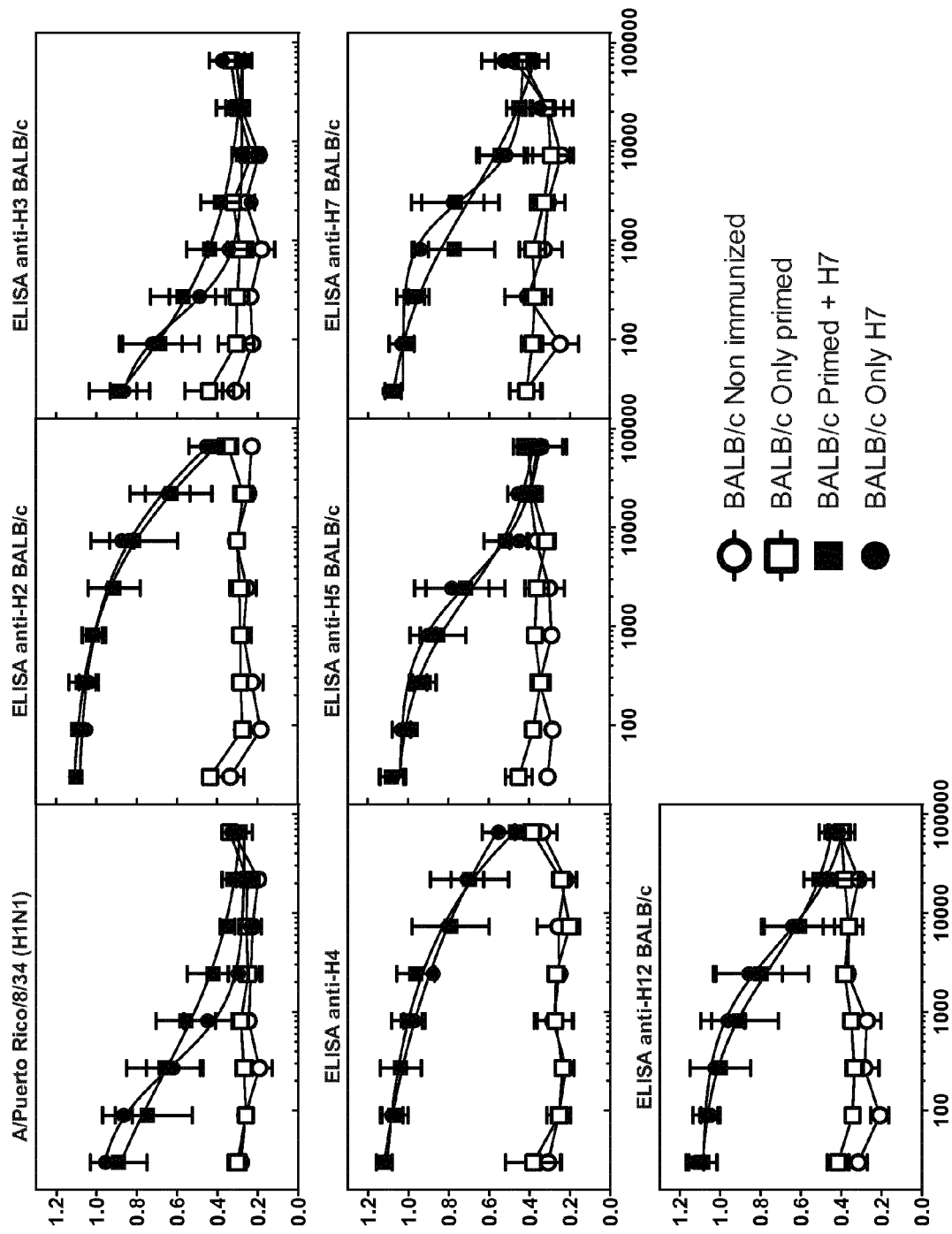
FIG. 2 shows the neutralizing titers of mAb 1.12 and 3.1.
Figure 3:
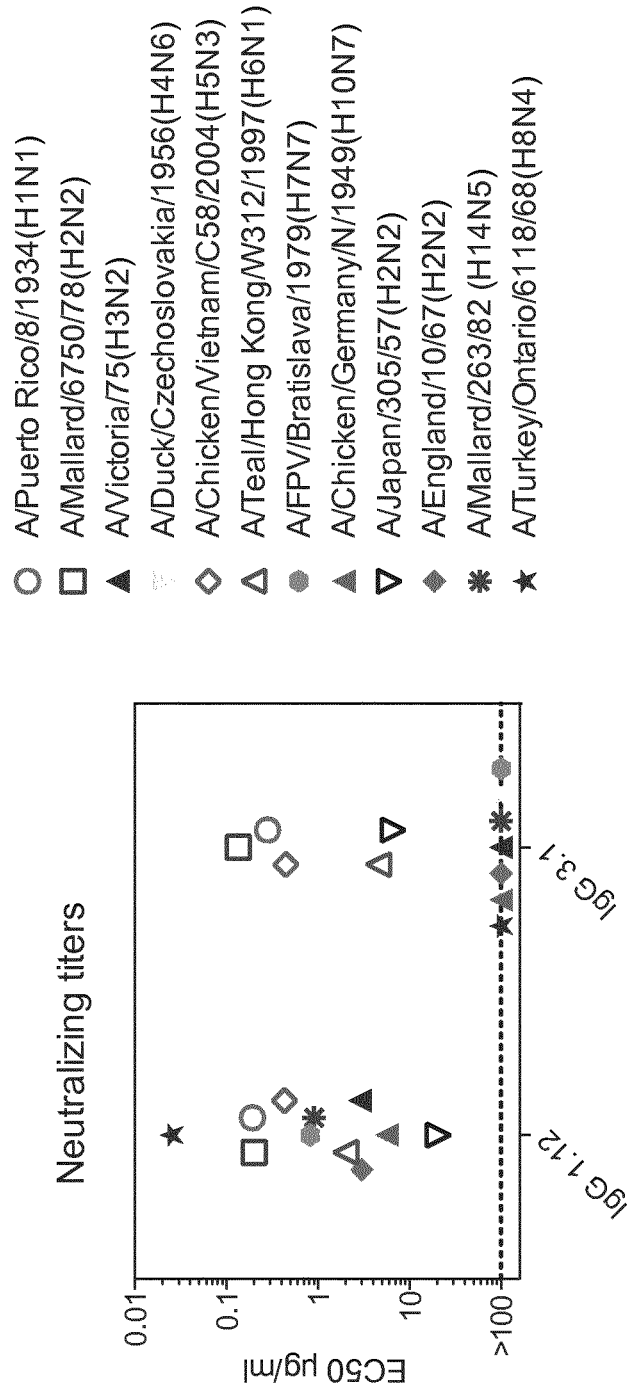
FIG. 3 shows results of ELISA determination of antibodies raised in mice by immunization with the antigen described herein (see Example 4).
Figure 4:
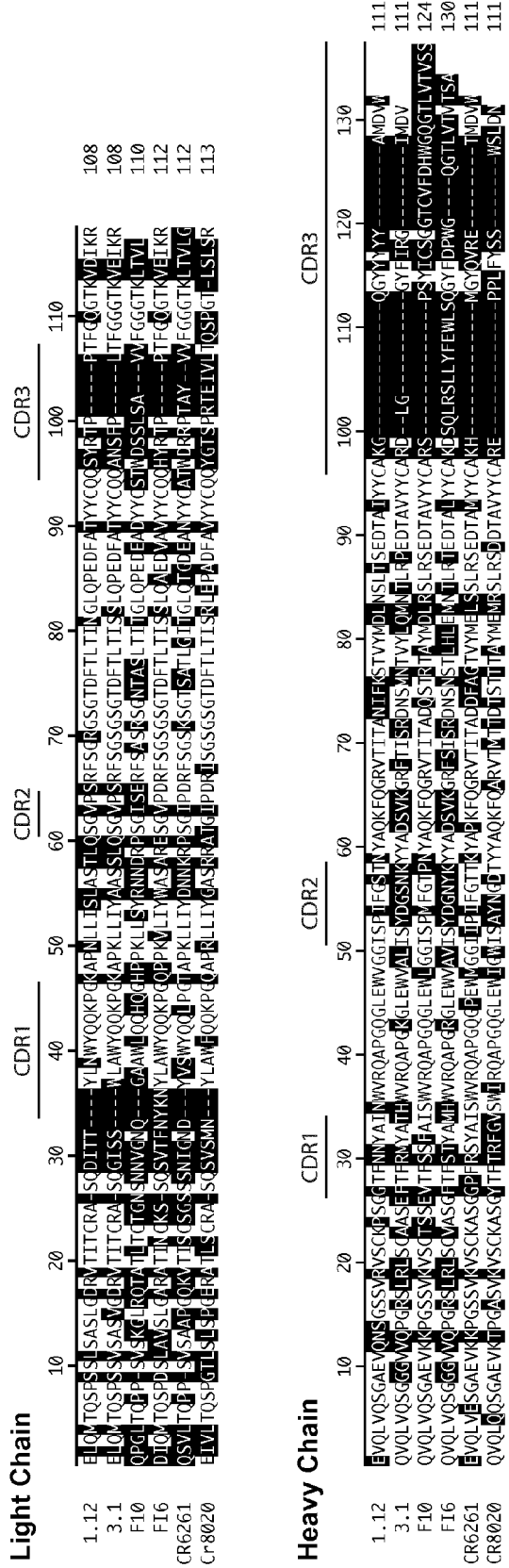

FIG. 4 shows an amino acid sequence comparison of broadly neutralizing monoclonal antibodies. The following respective light and heavy chain sequences are shown: mAb 1.12 (SEQ ID NOs 7 and 13), mAb 3.1 (SEQ ID NOs 8 and 14), mAb F10 (SEQ ID NOs 9 and 15), mAb F16 (SEQ ID NOs 10 and 16), mAb CR6261 (SEQ ID NOs 11 and 17), and CR8020 (SEQ ID NOs 12 and 18).

Figure 5:
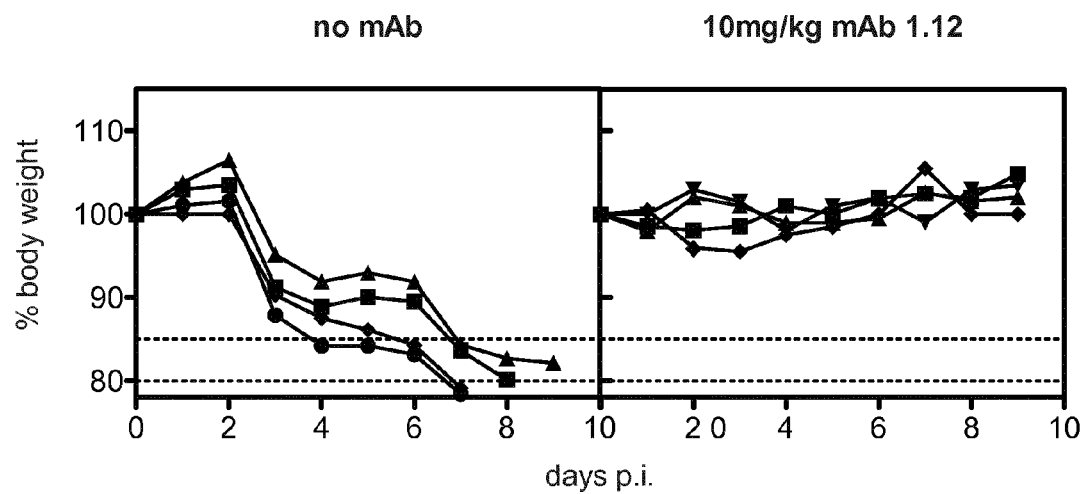

FIG. 5 shows results of a passive immunization experiment in mice.

EXAMPLE 1

In the instant invention isolation and characterization of two monoclonal heterosubtypic antibodies is described that both have been isolated by phage display. One of these antibodies, mAb1.12, bound and neutralized all influenza A viruses tested so far. These include A/Puerto Rico/8/1934 (H1N1), A/California/7/2009(H1N1), A/Japan/305/57 (H2N2), A/Mallard/6750/1978(H2N2), A/Victoria/1975 (H3N2), A/Perth/16/2009(H3N2), A/Duck/Czechoslovakia/1956(H4N6), A/Chicken/Vietnam/C58/2004(H5N3), A/Teal/Hong Kong/W312/97(H6N1), A/FPV/Bratislava/79 (H7N7), A/Turkey/Ontario/6118/68 (H8N4), A/HongKong/1073/97(H9N7), A/Chicken/Germany/N/49(H10N7), A/Duck/Memphis/546/74(H11N9), A/Duck/Alberta/60/76 (H12N5), A/Gull/MD/704/77(H13N6), A/Mallard/263/82 (H14N5) and A/Shearwater/Australia/2576/79(H15N9) and thus also encompasses viruses expressing HA subtypes belonging to group 2 (FIG. 1). The concentrations resulting in half-maximal neutralization have been plotted in FIG. 3, and indicate that most viruses are neutralized at single-digit-μg concentrations, if not at below 1 μg/ml.

Another other antibody derived from the method according to the invention, mAb 3.1, binds to recombinant H1, H2, and H5 and neutralizes viruses the viruses A/Puerto Rico/8/1934(H1N1), A/Mallard/6750/1978(H2N2), A/Japan/305/57(H2N2), A/Chicken/Vietnam/C58/2004(H5N3), and A/Teal/Hong Kong/W312/1997(H6N1). However, it failed at neutralizing viruses belonging to group 2 (i.e. A/Victoria/1975(H3N2), A/Duck/Czechoslovakia/1956(H4N6), and A/FPV/Bratislava/1979(H7N7) (FIG. 2). Since the heavy chain of this antibody is not encoded by the IGHV1-69 germline it is quite possible that the epitope of mAB 3.1 may represent a novel conserved area on the HA surface. This notion is also supported by competition data suggesting that it's epitope is only partially overlapping with that of mAb C179, and that mAb3.1 was able to bind to unprocessed HA proteins, indicating that its epitope is not affected by conformational changes ensuing the proteolytic cleavage.

The antibody concentrations resulting in neutralization of the indicated strains are depicted in FIG. 3. A dashed line was used to indicate highest antibody concentration used (100 μg/ml).

Method: Each well of a 96-well plate was seeded with $2\times10^4$ MDCK cells in a volume of 100 μL of DMEM/BSA (Dubleco's modified Eagle Medium supplemented with 50 U/ml Penicillin, 50 μg/ml Streptomycin, 0.05 mM Glutamine, 0.2% BSA, and 20 mM HEPES buffer pH 7.2-7.5) one day before the assay. Cells were allowed to settle at 37° C./5% $CO_2$ over night before 2- or 3-fold serial dilutions of purified monoclonal antibodies were prepared in triplicates in DMEM/BSA medium, starting at 300 μg/ml. 20 μl of these antibody dilutions were then mixed with 40 μl of DMEM/BSA containing the equivalent of 3 multiplicities of infection of virus, and incubated at 37° C./$CO_2$ for 2 h. After this incubation period, medium on cells was replaced with the virus/antibody mixture, and infection was allowed to proceed at 37° C./5% $CO_2$ for 1 h. The antibody/virus mixture was then aspirated and cells were washed once with 100 μl of PBS. Fresh DMEM/BSA medium was added to cells that were then incubated at 37° C./CO2 for 4.5 to 7 hours, depending on the virus stain used. After incubation, supernatant was aspirated, and cells were fixed by the addition of 150 μl methanol. Fifteen minutes later, methanol was removed, and cells were washed 3 times with 200 μl of PBS. For the staining, 50 μl of PBS containing 1% BSA and 3 μg/ml of FITC-labeled monoclonal antibody HB-65 (ATCC: HB-65, produced and labeled in house according to standard methods) was added to the fixed cells and incubated at 4° over night. Cells were then washed 3 times with PBS and nucleic acids were stained using DAPI or a comparable dye according to the manufacturers recommendations. After 15 minutes, cells were washed another 3 times with 200 μl of PBS, and both FITC and DAPI florescence was determined at multiple locations in each well using a PerkinElmer EnVision Plate reader. As final value for each well, the average of all measuring points was taken. Background-correction, normalization and non-linear regression of the titration course were performed in Prism 5 (Graphpad Software, Inc), and data points are depicted as mean with error bars corresponding to the standard deviation of the triplicates.

EXAMPLE 2

A detailed analysis of the V-region of both monoclonal antibodies is outlined in Table 1 and Table 2 for the Ig heavy and light chain, respectively. It further emphasizes that mAb 1.12 and 3.1 are completely distinct antibody entities as neither the V, D, J segment usage nor the N-nucleotide addition indicate a common ancestor or shared patterns. When compared to their respective germline genes, it becomes apparent that the light chain of mAb 3.1 does not display somatic hypermutation. The reason for this observation remains elusive as at this point, it is not known whether the light chain of mAb3.1 is involved in antigen binding at all. The heavy chain of mAb3.1 does display hypermutation, but to a lesser extent compared to that of mAb1.12. It is noteworthy that these mutations focus on CDR-H1, and FR-H3 region that both have been shown to interact with HA. Also the light chain of mAb 1.12 displays somatic hypermutation, indicating that it may have been subjected to affinity maturation in vivo. As for the light chain of mAb 3.1, a contribution of the light chain of mAb 1.12 to the binding of the antibody is speculative. Regarding the fact that several antibodies were isolated with exactly the same heavy chain as mAb 1.12 but paired to half a dozen different light chains, it may seem that the impact of the light chain is only minor if present at all.

For the preparation of the phage display library, 2×10⁷ frozen peripheral blood monocytes were thawed and B-cells isolate using magnetic beads decorated against CD22 (Miltenyi Biotec, cat. 130-046-401). Total RNA was extracted, reverse transcriptase PCR was performed according to Barbas et al. (see above). Amplified V(D)J regions were modified to be expressed on the phage surface cloned into the pComb-3× vector. Following transformation of *E. Coli* bacteria, phages were rescued by superinfection of the transformed bacteria with a M13-derived helper phage The panning antigen was linked to biotin via a thioreactive reactive but cleavable linker (Pierce EZ-Link HPDP-Biotin cat. 21341). About 13 µg of biotinylated antigen was were then allowed to bind to 250 µL of streptavidin-coated magnetic beads (Promega Streptavidin MagneSphere Paramagnetic Particles cat Z5481), and were used for the 1st round of panning, for the second and subsequent rounds, 2 µg HA were allowed to bind 50 µl of beads. For panning of the phage library, $2.5 \times 10^{12}$ pfu of phages were allowed to bind to the indicated volume of magnetic beads (1st round). In further rounds phage input was varying depending on selection strategy and antigen. Following the binding beads were washed with TBS buffer containing 0.05% Tween to remove non-bound phages. The stringency (number) of washes was increased at each round. After the washing step, biotinylated antigen carrying phage species was cleaved of the beads using 100 mM DTT solution. Eluted phages were further used to infect XL1 F' strain and amplified overnight at each round in presence of VCSM helper phage. Amplified phages were PEG-precipitated and used as input for following rounds of selection. After 4th round of selection phage infected XL1 F' cells were spread on LB amp100 agar plate and resulting bacterial clones were used to rescue phages. Phage clones were further tested on ELISA for cross-reactivity to several HA subtypes.

TABLE 1

V, D and J Segment usage and N-nucleotide addition for the mAb1.12 and 3.1 heavy chains, as determined by the algorithms provided by IMGT/V-QUEST

| | V-segment | N1 | D segment | N2 | J segment |
|---|---|---|---|---|---|
| mAb 1.12 | VH1-69*06 | aag | D5-5*01 | a | JH6*02 |
| mAb 3.1 | VH3-30*04 | | D3-9*01 | tcataaggggcattatg [1) | JH4*01 |

[1)] the N2 N nucleotide addition of mAB 3.1 is SEQ ID 5 of the sequence protocol.

TABLE 2

V and J segment usage for the mAb 1.12 and 3.1 light chains, as determined by the algorithms provided by IMGT/V-QUEST.

| | V segment | J segment |
|---|---|---|
| mAb 1.12 | VK1-39*01 | JK2*01 |
| mAb 3.1 | VK1-12*01 | JK4*01 |

EXAMPLE 3

Biotin-Mediated Immobilization

Thioreacitive biotin with a flexible linker of 24.7 Å (Pierce 21334, EZ-Link Iodoacetyl-PEG2-Biotin) was used for site-specific apical biotinlyation. Trigonometric calculations indicate that biotinylated HA trimers can either bind via one or two biotin molecules to each side of the avidin tetramer. Depending on the orientation by which the avidin molecules are attached to the solid surface, however, only one side of the avidin molecule may be available to bind biotinylated HA molecules.

Biotinylated HA proteins were used to decorate avidin-coated plastic plates, or strepavidin-coated magnetite beads for phage display and immunization experiments. The magnetite beads (Promega Z5482) have a surface area of 100-150 m² per mg of drained beads that can bind 1×10⁹ mols of biotin. This corresponds to 6×10¹⁴ biotin molecules. Dividing this surface area by the number of biotin molecules, a theoretical area of $1.66 \times 10^{-13}$ m² is at each biotin molecule's disposal resulting in a theoretic distance of at least 0.4 µm between each biotin molecule. Assuming that an average of two biotin-molecules are bound by one streptavidin molecule, this distance would double.

Thus, these calculations lead to the conclusion that a dense packing, as observed on virions, is unlikely to prevent antibodies from lateral access to streptavidin-bound HA molecules. However, apical access to the proteins is most likely prevented by biotin-mediated liking to avidin, as the diameter of a fab fragment is around 40 to 50 Å, too big to be accommodated in between the HA and avidin molecules.

EXAMPLE 4

Preparation of the Antigen

HA proteins were recombinantly expressed into the supernatant of SF9 insect cells using recombinant baculoviruses prepared either with the BacToBac (Invitrogen) or the BaculoGold (BD Biosciences) system according to the manufacturers recommendation. To assure secretion and proper folding, all expression constructs were prepared such that the influenza leader sequence was replaced with the leader sequence from the Baculovirus gp67 protein, and that the viral transmembrane region and the intracellular portion were replaced with a trimerization domain and a polyhistidin tag (Stevens et al. Science 312, 404-410 (2006)). Recombinant proteins were purified by affinity chromatography using Ni-NTA-Agarose columns according to the manufacturers instruction. First supernatant containing expressed protein was cleared by centrifugation and filtered before it was applied on NiNTA column (0.6 mL of packed resin) and passed using gravity flow. The column was then washed with 40 mL of wash buffer 2 (50 mM NaH2PO₄, 300 mM NaCl, 40 mM imidazole pH 8) buffer. Protein was eluted from column with 6 mL of elution buffer (50 mM NaH2PO₄, 300 mM NaCl, 250 mM imidazole pH 8) and concentrated.

One exemplary vector used to express the vaccine antigen is shown as SEQ ID 6.

Shielding of the Apical Epitopes by Magnetic Beads

For the preparation of inverted immobilized HA antigens, protein was dialysed 2×2.h against 10 mM Tris/50 mM NaCl pH 8 containing 1 mM of DTT to reduce the recombinant apical but not the internal cysteine residues. After dialysis, DTT was added to a final concentration of 4 mM and protein was incubated for another 15 min before it was allowed to bind Ni-NTA Agarose affinity column via its His-tag. Proteins immobilized on the column were then washed before they were incubated with freshly prepared 0.4 mM EZ-link Biotin-HPDP or 0.2 mM EZ-link Iodoacetyl—PEG2-Biotin (Pierce) in Ni wash buffer 1 (50 mM $NaH2PO_4$, 300 mM NaCl, pH 8) and the coupling reaction was allowed to proceed for 1.5 to 2 h in the dark. Unincorporated Biotin was then removed from the column and immobilized proteins washed with 10 ml of wash buffer 1. Washed proteins were then eluted from the column using elution buffer For the preparation of antigen beads, 50-70 μg of biotinylated protein were incubated with 1 mL of SAV magnetic beads for 15 minutes before non-incorporated proteins were removed by washing with TBS (before coupling HAs were digested for 1 h at RT with trypsing 10 ng trypsin/1 μg HA).

EXAMPLE 5

Immunization

Groups of 5 female C57Bl/6 or BALB/c mice (Charles River Laboratories) aged 6-8 weeks were primed subcutaneously with 1.5 μg hemagglutinin from A/California/7/2009 (H1N1), A/Perth/16/2009 (H3N2) and B/Brisbane/60/2009 (Crucell Inflexal V vaccine) in a volume of 100 μl PBS, followed by intraperitoneal injection of 50 μg purified and coupled antigen in a volume of 200 μl PBS at weeks 4 and 8. Alternatively, a group of mice received only the priming immunization and another group only the two purified antigen injections. Blood was collected before each immunization and at week 12.

Serum was drawn from immunized mice and analyzed for binding to antigen-coated microtitre wells (secondary antibody anti-mouse). For preparation of antigen, see Example 4.

EXAMPLE 6

Protection Study

Mice (6 to 12 weeks) were administered 10 mg/kg of purified human monoclonal antibody i.p. three hours before the infection. For the infection, mice were anesthetized, and $10^3$ TCID50 of A/Puerto Rico/8/1934(H1N1) was administered intra nasally in a volume of 25 μl. Body weight was determined daily, and mice were taken out of the experiment as soon as their weight loss exceeded 20%. (See FIG. 5)

The invention claimed is:

1. A polypeptide comprising the amino acid sequences encoded by nucleic acid sequences SEQ ID NO: 01 and SEQ ID NO: 02, or the amino acid sequences encoded by nucleic acid sequences SEQ ID NO: 03 and SEQ ID NO: 04.

2. A polypeptide according to claim 1, wherein the polypeptide comprises the amino acid sequences encoded by nucleic acid sequences SEQ ID NO: 01 and SEQ ID NO: 02, and wherein the polypeptide is capable of neutralizing 5 subtypes of influenza A virus, two of which subtypes are group 1 subtypes and two of which are group 2 subtypes.

3. A polypeptide according to claim 2, where the neutralized subtypes comprise
 a. H1, H2, H5 and H3, or
 b. H1, H2, H5 and H4, or
 c. H1, H2, H3 and H4, or
 d. H1, H2, H3 and H7, or
 e. H1, H2, H3, H4 and H7, or
 f. H1, H2 and H3.

4. A polypeptide according to claim 2, capable of neutralizing influenza A virus of
 a. 2 group 1 subtypes and 5 or 6 group 2 subtypes, or
 b. 3 group 1 subtypes and 5 or 6 group 2 subtypes, or
 c. 4 group 1 subtypes and 2, 3, 4, 5 or 6 group 2 subtypes, or
 d. 5 group 1 subtypes and 2, 3, 4, 5 or 6 group 2 subtypes, or
 e. 6 group 1 subtypes and 2, 3, 4, 5 or 6 group 2 subtypes, or
 f. 7 group 1 subtypes and 2, 3, 4, 5 or 6 group 2 subtypes, or
 g. 8 group 1 subtypes and 2, 3, 4, 5 or 6 group 2 subtypes, or
 h. 9 group 1 subtypes, and 2, 3, 4, 5 or 6 group 2 subtypes.

5. A polypeptide according to claim 1, comprising a polypeptide sequence encoded by variable region germline gene IGHV1-69.

6. A polypeptide according to claim 2, being capable of neutralizing influenza A virus from subtypes:
 H1N1, H2N2, H4N6, H5N3, H6N1, H11N9, H12N5, H13N6 and
 H3N2, H7N7, H10N7, H15N9.

7. A polypeptide according to claim 1, wherein the polypeptide is a gamma immunoglobulin.

8. A polypeptide according to claim 1, for use in a method for inhibition of influenza A infection.

9. A polypeptide according to claim 1 as part of a kit or device for diagnosis of influenza A infection.

* * * * *

SEQUENCE LISTING

<160> NUMBER OF SEQ ID NOS: 18

<210> SEQ ID NO 1
<211> LENGTH: 366
<212> TYPE: DNA
<213> ORGANISM: Homo sapiens

<400> SEQUENCE: 1

```
gaggtgcagc tggtgcagtc tggggctgag gtgcagaact ctgggtcctc ggtgagggtc      60
tcctgcaaac cttctggagg caccttcaac aactatgcta tcaactgggt gcgacaggcc     120
cctggacaag gacttgagtg ggtgggaggg atcagcccta tctttggttc aacaaactac     180
gcacagaagt tccagggcag agtcacgatt accgcgaaca tattcaagag cacagtctac     240
atggacctga cagcctgac atctgaggac acggccatat attactgtgc gaaaggccag     300
ggatactact actattacgc tatggacgtc tggggccaag gcaccctggt caccgtctcc     360
cctgcc                                                                366
```

<210> SEQ ID NO 2
<211> LENGTH: 324
<212> TYPE: DNA
<213> ORGANISM: Homo sapiens

<400> SEQUENCE: 2

```
gagctccaga tgacccagtc tccgtcctcc ctgtctgcat ctctaggaga cagagtcacc      60
atcacttgcc gggcaagtca ggacattacc acctatttaa attggtatca acagaaacca     120
gggaaagccc ctaacctcct gatctctctt gcatccactt tacaaagtgg ggtcccatca     180
aggttcagtg gcagggggatc tgggacagat ttcactctca ccatcaacgg tctccaacct     240
gaagattttg caacttacta ctgtcaacag agttacagga cccctccgac gttcggccaa     300
gggaccaagg tggacatcaa gcga                                            324
```

<210> SEQ ID NO 3
<211> LENGTH: 369
<212> TYPE: DNA
<213> ORGANISM: Homo sapiens

<400> SEQUENCE: 3

```
caggtgcagc tggtgcagtc tggggggaggc gtggtccagc ctgggaggtc cctgagactc    60
tcctgtgcag cctctgaatt caccttcaga atgtatgcta cccactgggt ccgccaggct   120
ccaggcaagg ggctggagtg ggtggctctt atctcatatg atggaagtaa taaatactat   180
gcagactccg tgaagggccg attcaccatc tccagagaca attccatgaa cacggtgtat   240
ctgcaaatga acaccctgag acctgaggac acggctgtct attactgtgc gagagattta   300
ggaggttatt tcataagggg cattatggac gtctggggcc aaggaaccct ggtcaccgtc   360
tcctcagcc                                                            369

<210> SEQ ID NO 4
<211> LENGTH: 324
<212> TYPE: DNA
<213> ORGANISM: Homo sapiens

<400> SEQUENCE: 4
gagctccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccgctcac tttcggcgga   300
gggaccaagg tggagatcaa acga                                           324

<210> SEQ ID NO 5
<211> LENGTH: 17
<212> TYPE: DNA
<213> ORGANISM: homo sapiens

<400> SEQUENCE: 5
tcataagggg cattatg                                                    17

<210> SEQ ID NO 6
<211> LENGTH: 11387
<212> TYPE: DNA
<213> ORGANISM: baculovirus

<400> SEQUENCE: 6
aagctttact cgtaaagcga gttgaaggat catatttagt tgcgtttatg agataagatt    60
gaaagcacgt gtaaaatgtt tcccgcgcgt tggcacaact atttacaatg cggccaagtt   120
ataaaagatt ctaatctgat atgttttaaa acaccttttgc ggcccgagtt gtttgcgtac   180
gtgactagcg aagaagatgt gtggaccgca gaacagatag taaaacaaaa ccctagtatt   240
ggagcaataa tcgatttaac caacacgtct aaatattatg atggtgtgca ttttttgcgg   300
gcgggcctgt tatacaaaaa aattcaagta cctggccaga ctttgccgcc tgaaagcata   360
gttcaagaat ttattgacac ggtaaaagaa tttacagaaa agtgtcccgg catgttggtg   420
ggcgtgcact gcacacacgg tattaatcgc accggttaca tggtgtgcag atatttaatg   480
cacaccctgg gtattgcgcc gcaggaagcc atagatagat cgaaaaagc cagaggtcac   540 aaaattgaaa gacaaaatta cgttcaagat ttattaattt aattaatatt atttgcattc   600
tttaacaaat actttatcct attttcaaat tgttgcgctt cttccagcga accaaaacta   660
tgcttcgctt gctccgttta gcttgtagcc gatcagtggc gttgttccaa tcgacggtag   720
gattaggccg gatattctcc accacaatgt tggcaacgtt gatgttacgt ttatgctttt   780
ggttttccac gtacgtcttt tggccggtaa tagccgtaaa cgtagtgccg tcgcgcgtca   840
```

```
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
tttgcaacaa ctattgtttt ttaacgcaaa ctaaacttat tgtggtaagc aataattaaa   1680 tatggggaa catgcgccgc tacaacactc gtcgttatga acgcagacgg cgccggtctc   1740
ggcgcaagcg gctaaaacgt gttgcgcgtt caacgcggca acatcgcaa aagccaatag    1800 tacagttttg atttgcatat taacggcgat ttttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gttttttacga agcgatgaca   2520 tgaccccgt agtgacaacg atcacgccca aagaactgc cgactacaaa attaccgagt     2580
atgtcggtga cgttaaaact attaagccat ccaatcgacc gttagtcgaa tcaggaccgc   2640
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga aagaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
```

```
atcaaatccc aagatgtgta taaaccacca aactgccaaa aaatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aattttattt tcacataaac    3480
tagacgcctt gtcgtcttct tcttcgtatt ccttctcttt ttcattttc tcctcataaa     3540 aattaacata gttattatcg tatccatata tgtatctatc gtatagagta aatttttgt     3600 tgtcataaat atatatgtct tttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tccctttcct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atctatgcta    4140
ctagtaaatc agtcacacca aggcttcaat aaggaacaca caagcaagat ggtaagcgct    4200
attgttttat atgtgctttt ggcggcggcg gcgcattctg cctttgcggc ggatccagac    4260
aaaatttgcc ttggacatca tgctgtatca aatggcacca aggtaaacac actcactgag    4320
agaggagtag aagttgtcaa tgcaacagaa acagtggagc ggacaaacat ccccaaaatt    4380
tgctcaaaag ggaaaagaac cgttgatctt ggccaatgcg gactactggg gaccattacc    4440
ggacaacctc aatgtgacca atttctagaa ttttcagctg atttaataat cgagaggcgg    4500
gacgaaaatg atgtttgtta cccggggaaa tttgtgaatg gagaggcatt gcggcaaatc    4560
ctcagaaaat caggtgggat taacaaagaa acaatgggat tcacatacag tggaataaga    4620
accaatggaa caactagtgc gtgtagaaga tcaggatctt cattctatgc agaaatgaag    4680
tggctcctgt cagattgcga caatgctgct ttcccacaaa tgacgaaatc atacaaaaac    4740
acaaggagag aaccagctct gatagtctgg ggaatccatc attcaggatc aaccaccgag    4800
cagaccaaac tatatggaag tggaaataaa ctggtaacag tcggaagttc caaatatcag    4860
cagtcttttg tgccgagtcc agaaacacga ccacaagtaa atggccagtc cggacgaatt    4920
gattttcact ggttgatact ggattccaat gacacagtta cttttagttt caatggggct    4980
ttcatagctc cagatcgtgc tagcttcttg aagggaaagt ccatgggaat ccaaagcgat    5040
gtgcaggttg atgccaattg cgaaggggaa tgctaccaca gtggagggac cataacaagc    5100
agtttgccct tccaaaacat caacagcagg gcagttggca agtgtccaag atatgtaaaa    5160
caggaaagtc tattattggc aacagggatg aagaatgttc ccgaactttc caaaaaaaga    5220
agaaaaagag gcctgtttgg cgccatagcg gggtttattg aaaatggttg ggaaggtctg    5280
gtcgacggat ggtacggttt caggcatcag aatgcacaag gagaaggaac tgcagcagac    5340
tacaaaagca cccagtcggc aattgatcag ataaccggaa aattaaatag actcattgag    5400
aaaactaatc agcaatttga gctaatagat aatgaattca ctgaggtaga aaagcagatt    5460
ggcaatgtaa ttaactggac cagagactcc atcacagaag tatggtctta caatgctgaa    5520
cttctcgtgg caatggaaaa tcagcacact attgatctag ctgattcaga gatgaacaaa    5580
```

```
ttgtatgagc gagtgaggaa acaattgagg gaaaatgctg aggaagatgg cactggttgt    5640
tttgagattt tccacaaatg tgatgatgat tgtatggcta gtataaggaa caatacttat    5700
gatcacagca aatacagaga agaagcaatg caaaatagaa tacaaattga cccagtcaaa    5760
gatggcagcc tggtgccccg cggcagcccc ggcagcggct acatccccga ggcccccgc     5820
gacggccagg cctacgtgcg caaggacggc gagtgggtgc tgctgagcac cttcctgacc    5880
ggtcaccacc accaccacca ctgaggcggc cgctgcagat ctgatccttt cctgggaccc    5940
ggcaagaacc aaaaactcac tctcttcaag gaaatccgta atgttaaacc cgacacgatg    6000
aagcttgtcg ttggatggaa aggaaaagag ttctacaggg aaacttggac ccgcttcatg    6060
gaagacagct tccccattgt taacgaccaa gaagtgatgg atgttttcct tgttgtcaac    6120
atgcgtccca ctagacccaa ccgttgttac aaattcctgg cccaacacgc tctgcgttgc    6180
gaccccgact atgtacctca tgacgtgatt aggatcgtcg agccttcatg ggtgggcagc    6240
aacaacgagt accgcatcag cctggctaag aagggcggcg gctgcccaat aatgaacctt    6300
cactctgagt acaccaactc gttcgaacag ttcatcgatc gtgtcatctg ggagaacttc    6360
tacaagccca tcgtttacat cggtaccgac tctgctgaag aggaggaaat tctccttgaa    6420
gtttccctgg tgttcaaagt aaaggagttt gcaccagacg cacctctgtt cactggtccg    6480
gcgtattaaa acacgataca ttgttattag tacatttatt aagcgctaga ttctgtgcgt    6540
tgttgattta cagacaattg ttgtacgtat tttaataatt cattaaattt ataatcttta    6600
gggtggtatg ttagagcgaa aatcaaatga ttttcagcgt ctttatatct gaatttaaat    6660
attaaatcct caatagattt gtaaaatagg tttcgattag tttcaaacaa gggttgtttt    6720
tccgaaccga tggctggact atctaatgga ttttcgctca acgccacaaa acttgccaaa    6780
tcttgtagca gcaatctagc tttgtcgata ttcgtttgtg ttttgttttg taataaaggt    6840
tcgacgtcgt tcaaaatatt atgcgctttt gtatttcttt catcactgtc gttagtgtac    6900
aattgactcg acgtaaacac gttaaataaa gcttggacat atttaacatc gggcgtgtta    6960
gctttattag gccgattatc gtcgtcgtcc caaccctcgt cgttagaagt tgcttccgaa    7020
gacgattttg ccatagccac acgacgccta ttaattgtgt cggctaacac gtccgcgatc    7080
aaatttgtag ttgagctttt tggaattatt tctgattgcg ggcgttttg ggcgggtttc     7140
aatctaactg tgcccgattt taattcagac aacacgttag aaagcgatgg tgcaggcggt    7200
ggtaacattt cagacggcaa atctactaat ggcggcggtg gtggagctga tgataaatct    7260
accatcggtg gaggcgcagg cggggctggc ggcgaggcg gaggcggagg tggtggcggt      7320
gatgcagacg gcggtttagg ctcaaatgtc tctttaggca acacagtcgg cacctcaact    7380
attgtactgg tttcgggcgc cgttttggt ttgaccggtc tgagacgagt gcgatttttt      7440
tcgtttctaa tagcttccaa caattgttgt ctgtcgtcta aggtgcagc gggttgaggt      7500
tccgtcggca ttggtggagc gggcggcaat tcagacatcg atggtggtgg tggtggtgga    7560
ggcgctggaa tgttaggcac gggagaaggt ggtggcggcg gtgccgccgg tataatttgt    7620
tctggtttag tttgttcgcg cacgattgtg ggcaccggcg caggcgccgc tggctgcaca    7680
acggaaggtc gtctgcttcg aggcagcgct tggggtggtg gcaattcaat attataattg    7740
gaatacaaat cgtaaaaatc tgctataagc attgtaattt cgctatcgtt taccgtgccg    7800
atatttaaca accgctcaat gtaagcaatt gtattgtaaa gagattgtct caagctccgc    7860
acgccgataa caagcctttt cattttttact acagcattgt agtggcgaga cacttcgctg    7920
```

```
tcgtcgacgt acatgtatgc tttgttgtca aaaacgtcgt tggcaagctt taaaatattt   7980
aaaagaacat ctctgttcag caccactgtg ttgtcgtaaa tgttgttttt gataatttgc   8040
gcttccgcag tatcgacacg ttcaaaaaat tgatgcgcat caattttgtt gttcctatta   8100
ttgaataaat aagattgtac agattcatat ctacgattcg tcatggccac cacaaatgct   8160
acgctgcaaa cgctggtaca attttacgaa aactgcaaaa acgtcaaaac tcggtataaa   8220
ataatcaacg ggcgctttgg caaaatatct attttatcgc acaagcccac tagcaaattg   8280
tatttgcaga aaacaatttc ggcgcacaat tttaacgctg acgaaataaa agttcaccag   8340
ttaatgagcg accacccaaa tttataaaa atctatttta atcacggttc catcaacaac    8400
caagtgatcg tgatggacta cattgactgt cccgatttat ttgaaacact acaaattaaa   8460
ggcgagcttt cgtaccaact tgttagcaat attattagac agctgtgtga agcgctcaac   8520
gatttgcaca agcacaattt catacacaac gacataaaac tcgaaaatgt cttatatttc   8580
gaagcacttg atcgcgtgta tgtttgcgat tacggattgt gcaaacacga aaactcactt   8640
agcgtgcacg acggcacgtt ggagtatttt agtccggaaa aaattcgaca cacaactatg   8700
cacgtttcgt ttgactggta cgcggcgtgt taacatacaa gttgctaacc ggcggttcgt   8760
aatcatggtc atagctgttt cctgtgtgaa attgttatcc gctcacaatt ccacacaaca   8820
tacgagccgg aagcataaag tgtaaagcct ggggtgccta atgagtgagc taactcacat   8880
taattgcgtt gcgctcactg cccgctttcc agtcgggaaa cctgtcgtgc cagctgcatt   8940
aatgaatcgg ccaacgcgcg gggagaggcg gtttgcgtat tgggcgctct tccgcttcct   9000
cgctcactga ctcgctgcgc tcggtcgttc ggctgcggcg agcggtatca gctcactcaa   9060
aggcggtaat acggttatcc acagaatcag gggataacgc aggaaagaac atgtgagcaa   9120
aaggccagca aaaggccagg aaccgtaaaa aggccgcgtt gctggcgttt ttccataggc   9180
tccgccccc tgacgagcat cacaaaaatc gacgctcaag tcagaggtgg cgaaacccga   9240
caggactata aagataccag gcgtttcccc ctggaagctc cctcgtgcgc tctcctgttc   9300
cgaccctgcc gcttaccgga tacctgtccg cctttctccc ttcgggaagc gtggcgcttt   9360
ctcatagctc acgctgtagg tatctcagtt cggtgtaggt cgttcgctcc aagctgggct   9420
gtgtgcacga accccccgtt cagcccgacc gctgcgcctt atccggtaac tatcgtcttg   9480
agtccaaccc ggtaagacac gacttatcgc cactggcagc agccactggt aacaggatta   9540
gcagagcgag gtatgtaggc ggtgctacag agttcttgaa gtggtggcct aactacggct   9600
acactagaag gacagtattt ggtatctgcg ctctgctgaa gccagttacc ttcggaaaaa   9660
gagttggtag ctcttgatcc ggcaaacaaa ccaccgctgg tagcggtggt ttttttgttt   9720
gcaagcagca gattacgcgc agaaaaaaag gatctcaaga agatcctttg atcttttcta   9780
cggggtctga cgctcagtgg aacgaaaact cacgttaagg gattttggtc atgagattat   9840
caaaaaggat cttcacctag atccttttaa attaaaaatg aagttttaaa tcaatctaaa   9900
gtatatatga gtaaacttgg tctgacagtt accaatgctt aatcagtgag gcacctatct   9960
cagcgatctg tctatttcgt tcatccatag ttgcctgact ccccgtcgtg tagataacta   10020
cgatacggga gggcttacca tctggcccca gtgctgcaat gataccgcga gacccacgct   10080
caccggctcc agatttatca gcaataaacc agccagccgg aagggccgag cgcagaagtg   10140
gtcctgcaac tttatccgcc tccatccagt ctattaattg ttgccgggaa gctagagtaa   10200
gtagttcgcc agttaatagt ttgcgcaacg ttgttgccat tgctacaggc atcgtggtgt   10260
cacgctcgtc gtttggtatg gcttcattca gctccggttc ccaacgatca aggcgagtta   10320
```

```
catgatcccc catgttgtgc aaaaaagcgg ttagctcctt cggtcctccg atcgttgtca   10380
gaagtaagtt ggccgcagtg ttatcactca tggttatggc agcactgcat aattctctta   10440
ctgtcatgcc atccgtaaga tgcttttctg tgactggtga gtactcaacc aagtcattct   10500
gagaatagtg tatgcggcga ccgagttgct cttgcccggc gtcaatacgg gataataccg   10560
cgccacatag cagaacttta aaagtgctca tcattggaaa acgttcttcg gggcgaaaac   10620
tctcaaggat cttaccgctg ttgagatcca gttcgatgta acccactcgt gcacccaact   10680
gatcttcagc atctttttact ttcaccagcg tttctgggtg agcaaaaaca ggaaggcaaa   10740
atgccgcaaa aaagggaata agggcgacac ggaaatgttg aatactcata ctcttccttt   10800
ttcaatatta ttgaagcatt tatcagggtt attgtctcat gagcggatac atatttgaat   10860
gtatttagaa aaataaacaa ataggggttc cgcgcacatt tccccgaaaa gtgccacctg   10920
acgtctaaga aaccattatt atcatgacat taacctataa aaataggcgt atcacgaggc   10980
cctttcgtct cgcgcgtttc ggtgatgacg gtgaaaacct ctgacacatg cagctcccgg   11040
agacggtcac agcttgtctg taagcggatg ccggagcag acaagcccgt cagggcgcgt    11100
cagcgggtgt tggcgggtgt cggggctggc ttaactatgc ggcatcagag cagattgtac   11160
tgagagtgca ccatatgcgg tgtgaaatac cgcacagatg cgtaaggaga aaataccgca   11220
tcaggcgcca ttcgccattc aggctgcgca actgttggga agggcgatcg gtgcgggcct   11280
cttcgctatt acgccagctg cgaaagggg gatgtgctgc aaggcgatta agttgggtaa    11340
cgccagggtt ttcccagtca cgacgttgta aaacgacggc cagtgcc                 11387
```

<210> SEQ ID NO 7
<211> LENGTH: 108
<212> TYPE: PRT
<213> ORGANISM: Homo sapiens

<400> SEQUENCE: 7

```
Glu Leu Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Thr Thr Tyr
            20                  25                  30

Leu Asn Trp Tyr Gln Gln Lys Pro Gly Lys Ala Pro Asn Leu Leu Ile
        35                  40                  45

Ser Leu Ala Ser Thr Leu Gln Ser Gly Val Pro Ser Arg Phe Ser Gly
    50                  55                  60

Arg Gly Ser Gly Thr Asp Phe Thr Leu Thr Ile Asn Gly Leu Gln Pro
65                  70                  75                  80

Glu Asp Phe Ala Thr Tyr Tyr Cys Gln Gln Ser Tyr Arg Thr Pro Pro
                85                  90                  95

Thr Phe Gly Gln Gly Thr Lys Val Asp Ile Lys Arg
            100                 105
```

<210> SEQ ID NO 8
<211> LENGTH: 108
<212> TYPE: PRT
<213> ORGANISM: Homo sapiens

<400> SEQUENCE: 8

```
Glu Leu Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30
```

```
Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105
```

<210> SEQ ID NO 9
<211> LENGTH: 110
<212> TYPE: PRT
<213> ORGANISM: Homo sapiens

<400> SEQUENCE: 9

```
Gln Pro Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
            35                  40                  45

Ser Tyr Arg Asn Asn Asp Arg Pro Ser Gly Ile Ser Glu Arg Phe Ser
        50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Thr Trp Asp Ser Ser Leu
                85                  90                  95

Ser Ala Val Val Phe Gly Gly Gly Thr Lys Leu Thr Val Leu
            100                 105                 110
```

<210> SEQ ID NO 10
<211> LENGTH: 112
<212> TYPE: PRT
<213> ORGANISM: Homo sapiens

<400> SEQUENCE: 10

```
Asp Ile Gln Met Thr Gln Ser Pro Asp Ser Leu Ala Val Ser Leu Gly
1               5                   10                  15

Ala Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
            35                  40                  45

Lys Val Leu Ile Tyr Trp Ala Ser Ala Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys Arg
            100                 105                 110
```

<210> SEQ ID NO 11
<211> LENGTH: 112
<212> TYPE: PRT
<213> ORGANISM: Homo sapiens

<400> SEQUENCE: 11

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu Gly
            100                 105                 110

<210> SEQ ID NO 12
<211> LENGTH: 113
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Asn
            20                  25                  30

Tyr Leu Ala Trp Phe Gln Gln Lys Pro Gly Gln Ala Pro Arg Leu Leu
        35                  40                  45

Ile Tyr Gly Ala Ser Arg Arg Ala Thr Gly Ile Pro Asp Arg Ile Ser
50                  55                  60

Gly Ser Gly Ser Gly Thr Asp Phe Thr Leu Thr Ile Ser Arg Leu Glu
65                  70                  75                  80

Pro Ala Asp Phe Ala Val Tyr Tyr Cys Gln Gln Tyr Gly Thr Ser Pro
                85                  90                  95

Arg Thr Glu Ile Val Leu Thr Gln Ser Pro Gly Thr Leu Ser Leu Ser
            100                 105                 110

Arg

<210> SEQ ID NO 13
<211> LENGTH: 111
<212> TYPE: PRT
<213> ORGANISM: Homo sapiens

<400> SEQUENCE: 13

Glu Val Gln Leu Val Gln Ser Gly Ala Glu Val Gln Asn Ser Gly Ser
1               5                   10                  15

Ser Val Arg Val Ser Cys Lys Pro Ser Gly Gly Thr Phe Asn Asn Tyr
            20                  25                  30

Ala Ile Asn Trp Val Arg Gln Ala Pro Gly Gln Gly Leu Glu Trp Val
        35                  40                  45

Gly Gly Ile Ser Pro Ile Phe Gly Ser Thr Asn Tyr Ala Gln Lys Phe
50                  55                  60

Gln Gly Arg Val Thr Ile Thr Ala Asn Ile Phe Lys Ser Thr Val Tyr
65                  70                  75                  80

Met Asp Leu Asn Ser Leu Thr Ser Glu Asp Thr Ala Ile Tyr Tyr Cys

```
                         85                  90                  95

Ala Lys Gly Gln Gly Tyr Tyr Tyr Tyr Ala Met Asp Val Trp
            100                 105                 110

<210> SEQ ID NO 14
<211> LENGTH: 111
<212> TYPE: PRT
<213> ORGANISM: Homo sapiens

<400> SEQUENCE: 14

Gln Val Gln Leu Val Gln Ser Gly Gly Val Val Gln Pro Gly Arg
1               5                   10                  15

Ser Leu Arg Leu Ser Cys Ala Ala Ser Glu Phe Thr Phe Arg Met Tyr
                20                  25                  30

Ala Thr His Trp Val Arg Gln Ala Pro Gly Lys Gly Leu Glu Trp Val
            35                  40                  45

Ala Leu Ile Ser Tyr Asp Gly Ser Asn Lys Tyr Tyr Ala Asp Ser Val
        50                  55                  60

Lys Gly Arg Phe Thr Ile Ser Arg Asp Asn Ser Met Asn Thr Val Tyr
65                  70                  75                  80

Leu Gln Met Asn Thr Leu Arg Pro Glu Asp Thr Ala Val Tyr Tyr Cys
                85                  90                  95

Ala Arg Asp Leu Gly Gly Tyr Phe Ile Arg Gly Ile Met Asp Val
            100                 105                 110

<210> SEQ ID NO 15
<211> LENGTH: 124
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
1               5                   10                  15

Ser Val Lys Val Ser Cys Thr Ser Ser Glu Val Thr Phe Ser Ser Phe
                20                  25                  30

Ala Ile Ser Trp Val Arg Gln Ala Pro Gly Gln Gly Leu Glu Trp Leu
            35                  40                  45

Gly Gly Ile Ser Pro Met Phe Gly Thr Pro Asn Tyr Ala Gln Lys Phe
        50                  55                  60

Gln Gly Arg Val Thr Ile Thr Ala Asp Gln Ser Thr Arg Thr Ala Tyr
65                  70                  75                  80

Met Asp Leu Arg Ser Leu Arg Ser Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser Ser
        115                 120

<210> SEQ ID NO 16
<211> LENGTH: 130
<212> TYPE: PRT
<213> ORGANISM: Homo sapiens

<400> SEQUENCE: 16
```

-continued

Gln Val Gln Leu Val Gln Ser Gly Gly Val Val Gln Pro Gly Arg
1               5                   10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Ser Ile Ser Arg Asp Asn Ser Asn Ser Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
                115                 120                 125

Ser Ala
    130

<210> SEQ ID NO 17
<211> LENGTH: 111
<212> TYPE: PRT
<213> ORGANISM: Homo sapiens

<400> SEQUENCE: 17

Glu Val Gln Leu Val Glu Ser Gly Ala Glu Val Lys Lys Pro Gly Ser
1               5                   10                  15

Ser Val Lys Val Ser Cys Lys Ala Ser Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp
            100                 105                 110

<210> SEQ ID NO 18
<211> LENGTH: 111
<212> TYPE: PRT
<213> ORGANISM: Homo sapiens

<400> SEQUENCE: 18

Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Arg Phe
            20                  25                  30

Gly Val Ser Trp Ile Arg Gln Ala Pro Gly Gln Gly Leu Glu Trp Ile
        35                  40                  45

Gly Trp Ile Ser Ala Tyr Asn Gly Asp Thr Tyr Tyr Ala Gln Lys Phe
    50                  55                  60

Gln Ala Arg Val Thr Met Thr Thr Asp Thr Ser Thr Thr Thr Ala Tyr
65                  70                  75                  80

```
-continued

Met Glu Met Arg Ser Leu Arg Ser Asp Asp Thr Ala Val Tyr Tyr Cys
                85                  90                  95

Ala Arg Glu Pro Pro Leu Phe Tyr Ser Ser Trp Ser Leu Asp Asn
            100             105             110
```